(12) United States Patent
King et al.

(10) Patent No.: US 11,789,414 B2
(45) Date of Patent: *Oct. 17, 2023

(54) SYSTEMS AND METHODS FOR HOLISTIC LOW CARBON INTENSITY FUEL PRODUCTION

(71) Applicant: MARATHON PETROLEUM COMPANY LP, Findlay, OH (US)

(72) Inventors: Virginia King, Findlay, OH (US); Timothy J. Peterkoski, Findlay, OH (US); James R. Northrup, II, Findlay, OH (US); David Whikehart, Findlay, OH (US); Gregory Herold, Findlay, OH (US)

(73) Assignee: MARATHON PETROLEUM COMPANY LP, Findlay, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/082,256

(22) Filed: Dec. 15, 2022

(65) Prior Publication Data

US 2023/0205148 A1 Jun. 29, 2023

Related U.S. Application Data

(63) Continuation-in-part of application No. 17/583,450, filed on Jan. 25, 2022, now Pat. No. 11,635,735, and
(Continued)

(51) Int. Cl.
*C10G 9/00* (2006.01)
*C10G 47/36* (2006.01)
(Continued)

(52) U.S. Cl.
CPC ............ *G05B 13/042* (2013.01); *C10G 9/00* (2013.01); *C10G 47/36* (2013.01); *C10L 1/02* (2013.01); *C10L 1/04* (2013.01); *C10L 3/06* (2013.01); *C12M 21/12* (2013.01); *C12M 41/48* (2013.01); *C12P 7/06* (2013.01); *E21B 43/12* (2013.01); *E21B 43/25* (2013.01); *G01N 33/225* (2013.01); *G01N 33/28* (2013.01); *G05B 19/4189* (2013.01); *G06Q 30/018* (2013.01); *G06Q 50/06* (2013.01); *G06Q 50/30* (2013.01); *G08C 17/02* (2013.01); *C10G 2300/1011* (2013.01); *C10G 2300/4043* (2013.01); *C10L 2200/0469* (2013.01); *C10L 2200/0476* (2013.01); *C10L 2230/14* (2013.01); *C10L 2270/10* (2013.01); *C10L 2290/24* (2013.01); *C10L 2290/58* (2013.01); *G05B 2219/45076* (2013.01); *G06Q 10/083* (2013.01); *Y02P 20/151* (2015.11)

(58) Field of Classification Search
CPC .............. G05B 13/042; G05B 19/4189; G05B 2219/45076; C10G 9/00; C10G 47/36; C10G 2300/1011; C10G 2300/4043; C10L 1/02; C10L 1/04; C10L 3/06; C10L 2200/0469; C10L 2200/0476; C10L 2230/14; C10L 2270/10; C10L 2290/24; C10L 2290/58; C12M 21/12; C12M 41/48; C12P 7/06; E21B 43/12; E21B 43/25; G01N 33/225; G01N 33/28; G06Q 30/018; G06Q 50/06; G06Q 50/30; G06Q 10/083; G08C 17/02; Y02P 20/151
See application file for complete search history.

(56) References Cited

U.S. PATENT DOCUMENTS 7,797,205 B2  9/2010  Song et al.
8,354,065 B1 * 1/2013  Sexton ...................... B01J 8/26
                                               422/139
(Continued)

FOREIGN PATENT DOCUMENTS

AU        2020101782        9/2020
CN         10029645         7/2019
(Continued)

OTHER PUBLICATIONS

Elgowainy, Amgad et al., Energy Efficiency and Greenhouse Gas Emission Intensity of Petroleum Products at U.S. Refineries, Environ. Sci. Technol. 2014, 48, 7612-7624.
(Continued)

*Primary Examiner* — Ellen M McAvoy
*Assistant Examiner* — Chantel Graham
(74) *Attorney, Agent, or Firm* — Womble Bond Dickinson (US) LLP

(57) ABSTRACT

The present disclosure generally relates to systems and methods utilizing regenerative agriculture for the procurement, production, refinement and/or transformation of low carbon intensity transportation fuels, including low carbon intensity biodiesel and/or renewable diesel, low carbon intensity biogasoline, low carbon intensity aviation, marine and kerosene fuels as well as fuel oil blends, low carbon intensity ethanol, and low carbon intensity hydrogen, that may be beneficially commercialized directly to consumers. In further aspects, the systems and methods of the present disclosure advantageously generate low carbon intensity comestibles, including sustainably-sourced meal and/or feed. The disclosed systems and methods may be utilized and optimized such that the resulting fuels and foodstuffs are characterized by a reduction in greenhouse gas production and a diminution in the fertilizer, pesticide and water required for producing the associated crop feedstocks.

30 Claims, 9 Drawing Sheets

Related U.S. Application Data a continuation-in-part of application No. 17/456,246, filed on Nov. 23, 2021, which is a continuation-in-part of application No. 17/392,588, filed on Aug. 3, 2021, now Pat. No. 11,550,273, and application No. 18/082,256, which is a continuation-in-part of application No. 17/392,600, filed on Aug. 3, 2021, and a continuation-in-part of application No. 17/392,622, filed on Aug. 3, 2021, said application No. 17/456,246 is a continuation-in-part of application No. 17/392,600, filed on Aug. 3, 2021, and a continuation-in-part of application No. 17/392,567, filed on Aug. 3, 2021, now Pat. No. 11,270,393, and a continuation-in-part of application No. 17/392,622, filed on Aug. 3, 2021, said application No. 17/583,450 is a continuation of application No. 17/392,567, filed on Aug. 3, 2021, and application No. 18/088,256, which is a continuation-in-part of application No. 17/392,588, filed on Aug. 3, 2021, now Pat. No. 11,550,273.

(60) Provisional application No. 63/267,636, filed on Feb. 7, 2022, provisional application No. 63/265,686, filed on Dec. 17, 2021, provisional application No. 63/199,001, filed on Nov. 30, 2020, provisional application No. 63/113,186, filed on Nov. 12, 2020, provisional application No. 63/198,626, filed on Oct. 30, 2020, provisional application No. 63/066,912, filed on Aug. 18, 2020, provisional application No. 63/061,162, filed on Aug. 4, 2020.

(51) Int. Cl.
| | | |
|---|---|---|
| C10L 1/02 | (2006.01) | |
| C10L 1/04 | (2006.01) | |
| G08C 17/02 | (2006.01) | |
| C10L 3/06 | (2006.01) | |
| C12P 7/06 | (2006.01) | |
| G05B 13/04 | (2006.01) | |
| C12M 1/00 | (2006.01) | |
| C12M 1/36 | (2006.01) | |
| G05B 19/418 | (2006.01) | |
| G01N 33/22 | (2006.01) | |
| G01N 33/28 | (2006.01) | |
| G06Q 30/018 | (2023.01) | |
| G06Q 50/06 | (2012.01) | |
| E21B 43/12 | (2006.01) | |
| E21B 43/25 | (2006.01) | |
| G06Q 50/30 | (2012.01) | |
| G06Q 10/083 | (2023.01) | |

(56) References Cited

U.S. PATENT DOCUMENTS

| | | | |
|---|---|---|---|
| 10,605,411 | B2 | 3/2020 | Robbins et al. |
| 11,270,393 | B2 | 3/2022 | Whikehart et al. |
| 11,320,095 | B2 | 5/2022 | Rady et al. |
| 11,334,794 | B2 | 5/2022 | Celano et al. |
| 11,448,773 | B2 | 9/2022 | Bennett |
| 11,550,273 | B2 | 1/2023 | Whikehart et al. |
| 11,635,735 | B2 | 4/2023 | Whikehart et al. |
| 2009/0305360 | A1 | 12/2009 | Breneman et al. |
| 2010/0332273 | A1 | 12/2010 | Balasubramanian et al. |
| 2011/0093127 | A1 | 4/2011 | Kaplan |
| 2014/0218242 | A1 | 8/2014 | Platzer |
| 2017/0160118 | A1* | 6/2017 | Williams ............... H04L 67/12 |
| 2020/0291316 | A1 | 9/2020 | Robbins et al. |
| 2020/0372375 | A1 | 11/2020 | Pathak et al. |
| 2021/0156521 | A1 | 5/2021 | Aschinger et al. |
| 2022/0041974 | A1 | 2/2022 | Whikehart et al. |
| 2022/0042406 | A1 | 2/2022 | Whikehart et al. |
| 2022/0083017 | A1 | 3/2022 | Whikehart |
| 2022/0267810 | A1 | 8/2022 | Lyubovsky et al. |
| 2022/0398448 | A1 | 12/2022 | Jayaraman et al. |
| 2023/0082127 | A1 | 3/2023 | Whikehart et al. |
| 2023/0259080 | A1 | 8/2023 | Whikehart et al. |

FOREIGN PATENT DOCUMENTS

| | | |
|---|---|---|
| CN | 111062568 | 4/2020 |
| EP | 3739295 | 11/2020 |
| IN | 12812008 | 8/2010 |
| WO | 2006083273 | 8/2006 |
| WO | 2021152205 | 8/2021 |
| WO | 2022157589 | 7/2022 |

OTHER PUBLICATIONS

Argonne National Laboratory, General Motors Corporation, Well-to-Wheel Energy Use and Greenhouse Gas Emissions of Advanced Fuel/Vehicle Systems, North American Analysis, vol. 1, Apr. 2001.
Gordon, Deborah, et al., Know Your Oil, Creating a Global Oil-Climate Index, 2015 Carnegie Endowment for International Peace.
BP, BP sets ambition for net zero by 2050, fundamentally changing organisation to deliver, Feb. 12, 2020.
BP, from IOC to IEC, Second quarter 2020 financial results and strategy presentation, Aug. 2020.
BP p.l.c. Group results, Second quarter and half year 2020, London, Aug. 4, 2020.
Brinkman et al., Well-to-Wheels Analysis of Advanced Fuel/Vehicle Systems—A North American Study of Energy Use, Greenhouse Gas Emissions, and Criteria Pollutant Emissions, May 2005.
El-Houjeiri, Hassan M. et al., Oil Production Greenhouse Gas Emissions Estimator, Jun. 5, 2017.
Argonne National Laboratory, Cradle-to-Grave Lifecycle Analysis of U.S. Light-Duty Vehicle-Fuel Pathways: A Greenhouse Gas Emissions and Economic Assessment of Current (2015) and Future (2025-2030) Technologies, ANL/ESD-16/7, Rev. 1, Sep. 2016.
Forman, Grant S. et al., U.S. Refinery Efficiency: Impacts Analysis and Implications for Fuel Carbon Policy Implementation, Environmental Science & Technology, 2014.
Malins, Chris et al., Crude Oil Greenhouse Gas Emissions Calculation Methodology for the Fuel Quality Directive, The International Council on Clean Transportation to the European Commission Directorate-General for Climate Action, 2014.
Nimana, Balwinder et al., Life cycle assessment of greenhouse gas emissions from Canada's oil sands-derived transportation fuels, Department of Mechanical Engineering, University of Alberta, 2015.
Ramachandran, Srikkanth et al., Well to wheel analysis of low carbon alternatives for road traffic, Energy Environ. Sci. 2015, 8, 3313.
Toyota Motor Corporation, Well-to-Wheel Analysis of Greenhouse Gas Emissions of Automotive Fuels in the Japanese Context, Nov. 2004.
Vineyard, Donald, et al., A Comparison of Major Petroleum Life Cycle Models, Clean Technol Environ Policy. Apr. 2017; 19(3): 735-747. doi:10.1007/s10098-016-1260-6.
Riverol, C et al., A Non-linear Autoregressive Eternal Inputs (NARX) model for estimating the mixing volumes between patches in TRANSMIX, International Journal of Heat and Mass Transfer 127, 2018, 161-163.
Cheng, Lifei et al., Logistics for world-wide crude oil transportation using discrete event simulation and optimal control, Computers and Chemical Engineering 28, 2004, 897-911.
Bush, Amy et al., Iterative Optimization and Simulation of Barge Traffic on an Inland Waterway, Proceedings of the 2003 Winter Simulation Conference, Jan. 2004, 1751-1756.
Smith, Laurence Douglas et al., Simulation of alternative approaches to relieving congestion at locks in a river transport system, The Journal of the Operational Research Society, vol. 60, No. 4, Apr. 2009, 519-533.

(56) References Cited

OTHER PUBLICATIONS

Martins, Marcella Scoczynski Ribeiro et al., Discrete Event Simulation for Petroleum Transfers Involving Harbors, Refineries and Pipelines, Rio Pipeline 2009 Conference & Exposition, Sep. 2009.

* cited by examiner

SYSTEMS AND METHODS FOR HOLISTIC LOW CARBON INTENSITY FUEL PRODUCTION

CROSS REFERENCE TO RELATED APPLICATIONS

This application claims priority to, and the benefit of, U.S. Provisional Application No. 63/265,686, filed Dec. 17, 2021, titled "SYSTEMS AND METHODS FOR HOLISTIC LOW CARBON INTENSITY FUEL PRODUCTION," and U.S. Provisional Application No. 63/267,636, filed Feb. 7, 2022, titled "SYSTEMS AND METHODS FOR HOLISTIC LOW CARBON INTENSITY FUEL PRODUCTION," the disclosures of which are incorporated herein by reference in their entireties.

This application is a continuation-in-part of U.S. Non-Provisional application Ser. No. 17/456,246, filed Nov. 23, 2021, titled "SYSTEMS AND METHODS OF ALTERNATIVE ENERGY INTEGRATION WITH HYDROCARBON PRODUCTS," which claims priority to, and the benefit of, U.S. Provisional Application No. 63/199,001, filed Nov. 30, 2020, titled "SYSTEMS AND METHODS OF ALTERNATIVE ENERGY INTEGRATION WITH HYDROCARBON PRODUCTS," the disclosures of which are incorporated herein by reference in their entireties. U.S. Non-Provisional application Ser. No. 17/456,246 is also a continuation-in-part of U.S. Non-Provisional application Ser. No. 17/392,600, filed Aug. 3, 2021, titled "SYSTEMS AND METHODS FOR HOLISTIC LOW CARBON INTENSITY FUEL PRODUCTION," which claims priority to U.S. Provisional Application No. 63/061,162, filed Aug. 4, 2020, titled "SYSTEMS AND METHODS FOR HOLISTIC LOW CARBON INTENSITY FUEL PRODUCTION," U.S. Provisional Application No. 63/066,912, filed Aug. 18, 2020, titled "SYSTEMS AND METHODS FOR HOLISTIC LOW CARBON INTENSITY FUEL PRODUCTION," U.S. Provisional Application No. 63/198,626, filed Oct. 30, 2020, titled "SYSTEMS AND METHODS FOR HOLISTIC LOW CARBON INTENSITY FUEL AND HYDROGEN PRODUCTION," and U.S. Provisional Application No. 63/113,186, filed Nov. 12, 2020, titled "SYSTEMS AND METHODS FOR HOLISTIC LOW CARBON INTENSITY FUEL AND HYDROGEN PRODUCTION," the disclosures of which are incorporated herein by reference in its entirety. U.S. Non-Provisional application Ser. No. 17/456,246 is also a continuation-in-part of U.S. Non-Provisional application Ser. No. 17/392,567, filed Aug. 3, 2021, titled "SYSTEMS AND METHODS FOR HOLISTIC LOW CARBON INTENSITY FUEL PRODUCTION," which claims priority to U.S. Provisional Application No. 63/061,162, filed Aug. 4, 2020, titled "SYSTEMS AND METHODS FOR HOLISTIC LOW CARBON INTENSITY FUEL PRODUCTION," U.S. Provisional Application No. 63/066,912, filed Aug. 18, 2020, titled "SYSTEMS AND METHODS FOR HOLISTIC LOW CARBON INTENSITY FUEL PRODUCTION," U.S. Provisional Application No. 63/198,626, filed Oct. 30, 2020, titled "SYSTEMS AND METHODS FOR HOLISTIC LOW CARBON INTENSITY FUEL AND HYDROGEN PRODUCTION," and U.S. Provisional Application No. 63/113,186, filed Nov. 12, 2020, titled "SYSTEMS AND METHODS FOR HOLISTIC LOW CARBON INTENSITY FUEL AND HYDROGEN PRODUCTION," the disclosures of which are incorporated herein by reference in its entirety. U.S. Non-Provisional application Ser. No. 17/456,246 is also a continuation-in-part of U.S. Non-Provisional application Ser. No. 17/392,622, filed Aug. 3, 2021, titled "SYSTEMS AND METHODS FOR HOLISTIC LOW CARBON INTENSITY FUEL AND ETHANOL PRODUCTION," which claims priority to U.S. Provisional Application No. 63/061,162, filed Aug. 4, 2020, titled "SYSTEMS AND METHODS FOR HOLISTIC LOW CARBON INTENSITY FUEL PRODUCTION," U.S. Provisional Application No. 63/066,912, filed Aug. 18, 2020, titled "SYSTEMS AND METHODS FOR HOLISTIC LOW CARBON INTENSITY FUEL PRODUCTION," U.S. Provisional Application No. 63/198,626, filed Oct. 30, 2020, titled "SYSTEMS AND METHODS FOR HOLISTIC LOW CARBON INTENSITY FUEL AND HYDROGEN PRODUCTION," and U.S. Provisional Application No. 63/113,186, filed Nov. 12, 2020, titled "SYSTEMS AND METHODS FOR HOLISTIC LOW CARBON INTENSITY FUEL AND HYDROGEN PRODUCTION," the disclosures of which are incorporated herein by reference in its entirety.

This application is also a continuation-in-part of U.S. Non-Provisional application Ser. No. 17/392,600, filed Aug. 3, 2021, titled "SYSTEMS AND METHODS FOR HOLISTIC LOW CARBON INTENSITY FUEL PRODUCTION," which claims priority to U.S. Provisional Application No. 63/061,162, filed Aug. 4, 2020, titled "SYSTEMS AND METHODS FOR HOLISTIC LOW CARBON INTENSITY FUEL PRODUCTION," U.S. Provisional Application No. 63/066,912, filed Aug. 18, 2020, titled "SYSTEMS AND METHODS FOR HOLISTIC LOW CARBON INTENSITY FUEL PRODUCTION," U.S. Provisional Application No. 63/198,626, filed Oct. 30, 2020, titled "SYSTEMS AND METHODS FOR HOLISTIC LOW CARBON INTENSITY FUEL AND HYDROGEN PRODUCTION," and U.S. Provisional Application No. 63/113,186, filed Nov. 12, 2020, titled "SYSTEMS AND METHODS FOR HOLISTIC LOW CARBON INTENSITY FUEL AND HYDROGEN PRODUCTION," the disclosures of which are incorporated herein by reference in their entireties.

This application is also a continuation-in-part of U.S. Non-Provisional application Ser. No. 17/583,450, filed Jan. 25, 2022, titled "SYSTEMS AND METHODS FOR HOLISTIC LOW CARBON INTENSITY FUEL PRODUCTION," which is a continuation of U.S. Non-Provisional application Ser. No. 17/392,567, filed Aug. 3, 2021, titled "SYSTEMS AND METHODS FOR HOLISTIC LOW CARBON INTENSITY FUEL PRODUCTION," now U.S. Pat. No. 11,270,393, issued Mar. 8, 2022, which claims priority to U.S. Provisional Application No. 63/061,162, filed Aug. 4, 2020, titled "SYSTEMS AND METHODS FOR HOLISTIC LOW CARBON INTENSITY FUEL PRODUCTION," U.S. Provisional Application No. 63/066,912, filed Aug. 18, 2020, titled "SYSTEMS AND METHODS FOR HOLISTIC LOW CARBON INTENSITY FUEL PRODUCTION," U.S. Provisional Application No. 63/198,626, filed Oct. 30, 2020, titled "SYSTEMS AND METHODS FOR HOLISTIC LOW CARBON INTENSITY FUEL AND HYDROGEN PRODUCTION," and U.S. Provisional Application No. 63/113,186, filed Nov. 12, 2020, titled "SYSTEMS AND METHODS FOR HOLISTIC LOW CARBON INTENSITY FUEL AND HYDROGEN PRODUCTION," the disclosures of which are incorporated herein by reference in their entireties.

This application is also a continuation-in-part of U.S. Non-Provisional application Ser. No. 17/392,622, filed Aug. 3, 2021, titled "SYSTEMS AND METHODS FOR HOLISTIC LOW CARBON INTENSITY FUEL AND ETHANOL PRODUCTION," which claims priority to U.S. Provisional Application No. 63/061,162, filed Aug. 4, 2020, titled "SYSTEMS AND METHODS FOR HOLISTIC LOW CARBON INTENSITY FUEL PRODUCTION," U.S. Provisional Application No. 63/066,912, filed Aug. 18, 2020, titled "SYSTEMS AND METHODS FOR HOLISTIC LOW CARBON INTENSITY FUEL PRODUCTION," U.S. Provisional Application No. 63/198,626, filed Oct. 30, 2020, titled "SYSTEMS AND METHODS FOR HOLISTIC LOW CARBON INTENSITY FUEL AND HYDROGEN PRODUCTION," and U.S. Provisional Application No. 63/113,186, filed Nov. 12, 2020, titled "SYSTEMS AND METHODS FOR HOLISTIC LOW CARBON INTENSITY FUEL AND HYDROGEN PRODUCTION," the disclosures of which are incorporated herein by reference in their entireties.

This application is also a continuation-in-part of U.S. Non-Provisional application Ser. No. 17/392,588, filed Aug. 3, 2021, titled "SYSTEMS AND METHODS FOR HOLISTIC LOW CARBON INTENSITY FUEL PRODUCTION," which claims priority to U.S. Provisional Application No. 63/061,162, filed, Aug. 4, 2020, titled "SYSTEMS AND METHODS FOR HOLISTIC LOW CARBON INTENSITY FUEL PRODUCTION," U.S. Provisional Application No. 63/066,912, filed Aug. 18, 2020, titled "SYSTEMS AND METHODS FOR HOLISTIC LOW CARBON INTENSITY FUEL PRODUCTION," U.S. Provisional Application No. 63/198,626, filed Oct. 30, 2020, titled "SYSTEMS AND METHODS FOR HOLISTIC LOW CARBON INTENSITY FUEL AND HYDROGEN PRODUCTION," and U.S. Provisional Application No. 63/113,186, filed Nov. 12, 2020, titled "SYSTEMS AND METHODS FOR HOLISTIC LOW CARBON INTENSITY FUEL AND HYDROGEN PRODUCTION," the disclosures of which are incorporated herein by reference in their entireties.

FIELD OF DISCLOSURE

The present disclosure generally relates to systems and methods utilizing regenerative agriculture for the procurement, production, refinement and/or transformation of low carbon intensity transportation fuels, including but not limited to low carbon intensity renewable diesel, low carbon intensity biodiesel, low carbon intensity ethanol, and low carbon intensity hydrogen, that may be beneficially commercialized directly to consumers. In further aspects, the systems and methods of the present disclosure advantageously generate low carbon intensity comestibles, including sustainably-sourced meal and/or feed.

BACKGROUND

The unfavorable effects of the atmospheric release of greenhouse gases such as carbon dioxide ($CO_2$), methane ($CH_4$), nitrous oxide ($N_2O$), hydrofluorocarbons, gaseous sulfur compounds and perfluorinated chemicals have been widely attributed to climate change, which may include atmospheric and oceanic alterations. Greenhouse gases are often released during commercial and consumer activities that involve, e.g., the combustion of hydrocarbons, biofuels and other organic based fuels that may be utilized in endothermic processes and reactions. The quantification of greenhouse gases release, which may be measured as and/or attributable to consumer and/or industrial activities, may be assessed in terms of "carbon intensity" and "emission intensity," which beneficially provides for the measure of the greenhouse gases emitted per unit of activity or production. In terms of fuel and fuel additive production, processing and/or consumption, carbon intensity may be measured according to lifecycle greenhouse gases emitted per unit of energy, i.e. from 1) the planting and nurturing of seed that gives rise to crop feedstock, 2) the harvesting of the crop feedstock and manipulation of the same via crushing, fermenting, distilling, et al., for producing one or more biofuels and/or biofuel additives, 3) the isolation and/or acquisition of the biofuel and/or biofuel additive, 4) the delivery of the biofuel and/or biofuel additive to an end user (e.g., a consumer at a convenience store), and 5) the combustion of the biofuel and/or biofuel additive via the use of a vehicle.

In response to the use of traditional hydrocarbon based fuels for supplying energy, low carbon intensity energy strategies have often focused on the use of alternative, renewable sources such as wind, solar, hydrothermal and geothermal energy. For example, low carbon intensity renewable power may be produced at wind farms, solar farms, geothermal power plants and facilities, and hydrothermal or hydroelectric facilities. However, such farms and facilities are often geographically remote with regards to the consumers and commercial users targeted by these facilities.

Regenerative agricultural techniques and operations, which include regenerative farming, regenerative grazing, regenerative aquaculture and regenerative ranching, seek to reduce deleterious greenhouse gas emissions, promote carbon sequestration, and mitigate climate change by, inter alia, utilizing "cover crops" (e.g., grasses, legumes, brassicas and/or non-legume broadleaf crops), as well as reducing the need for common chemical and fuel-intensive agricultural practices such as tilling, traditional fertilizing, watering, herbicide and pest treatment strategies. Such techniques and operations can beneficially promote carbon sequestration, therefore reducing the carbon intensity and emission intensity associated with these practices, while adding further commercial value in the form of the production of crop-based comestibles and related products.

In view of the benefits of regenerative farming related to carbon biosequestration and the promotion of carbon bioavailability, and in further view of the geographic challenges associated with alternative/renewable energy delivery (which do not impart the added benefit of agricultural production associated with regenerative farming), Applicants have recognized a need for systems and methods based on regenerative agriculture and capable of providing consumers and commercial users with low carbon intensity transportation fuels, including renewable and low carbon diesel, renewable hydrocarbons such as renewable natural gas, biofuels containing bioethanol and low carbon intensity hydrogen through conventional pathways in which the resulting fuels and fuel additives are produced via targeted, strategic reductions of carbon emissions associated with the various stages of fuel and fuel additive selection, production, and transport. The present disclosure is directed to embodiments and aspects featuring such methods and systems.

SUMMARY

The present disclosure relates to systems and methods utilizing regenerative agriculture, including regenerative farming, for the procurement, production, refinement and/or transformation of low carbon intensity transportation fuels. In some embodiments, the present disclosure relates to a method to provide low carbon intensity (CI) transportation fuel, which may be obtained through one or more targeted reductions directed to carbon emissions (CE) and/or greenhouse gas emissions, where the method comprises determining, via a controller, a CI threshold for defining an upper limit for CI of transportation fuel to be provided to an end user location; determining, via the controller, two or more feedstocks that are procured at two or more sources, where the two or more feedstocks are selected based on their capacity for reducing CE and thereby maintaining the CI of the transportation fuel below the CI threshold. In alternative aspects, the method for providing low CI transportation fuel, including all related manipulations, determinations and implementations as disclosed herein, is performed in the absence of the controller. In certain embodiments, at least one of the two or more sources consists of a regenerative farm, a feedstock from the regenerative farm consisting of a crop selected from one or more of corn, soy beans, or other vegetables or grains that include a sufficient amount or amounts of oil, and determining, via the controller, a transportation pathway to transport the two or more feedstocks from the source to a transportation fuel production facility, where the transportation pathway is selected based on its capacity for reducing CE associated therewith such that the CI of the transportation fuel below the CI threshold is maintained.

In related embodiments, the controller is used to determine one or more transportation fuel production processes for reducing carbon emissions (CE) such that the carbon intensity (CI) of the transportation fuel is maintained below the CI threshold. For instance, the one or more transportation fuel production processes may be selected from a group including 1) powering at least a portion of transportation fuel production facility equipment with electricity generated proximal to the transportation fuel production facility via at least one renewable source, 2) burning renewable natural gas in a transportation fuel production facility furnace, 3) generating steam through renewable natural gas-fed or hydrogen-fed boilers, and 4) sequestering carbon dioxide ($CO_2$) that is directly and/or indirectly produced during the transportation fuel production process. In further aspects, the controller may be used to determine a distribution pathway for transporting a quantity of the transportation fuel from the transportation fuel production facility to the consumer or end user location, where the distribution pathway is advantageously selected on the basis of a reduction in associated carbon emissions such that the CI of the transportation fuel is maintained below the CI threshold.

The disclosed method may, in additional embodiments, encompass pre-processing of the feedstock from the regenerative farm, where pre-processing encompasses one or more of crushing, heat treating and/or enzymatically treating crop segregates for forming an oil, and processing the resulting oil into at least one renewable transportation fuel while simultaneously operating the selected one or more transportation fuel production processes, and blending the renewable transportation fuel with an additional transportation fuel to form a subsequent transportation fuel, which may consist of a transportation fuel suitable for use by a consumer or end user. In embodiments, the crushing, heat treating and/or enzymatically treating crop segregates for forming an oil may be performed in an intermediate facility that is, e.g., separated from one or both of the regenerative farming operation and/or biofuel plant, and is capable of one or more of crushing, cold pressing, fermenting and/or distilling one or more crop feedstocks. For instance, the intermediate facility may consist of a soybean crushing facility capable of crushing soybean feedstocks for producing one or more of soybean oil capable of being utilized or formulated into a transportation fuel, a consumable food product and/or an animal feed. In some aspects, the method may include determining, by the controller, the transportation fuel CI based on 1) a CI associated with procuring the selected feedstock at the source, 2) a CI associated with transporting the feedstock from the source to the transportation fuel production facility by use of the selected transportation pathway, 3) a CI associated with processing the feedstock into transportation fuel transportation fuel together with operating the one or more transportation fuel production processes, and 4) a CI associated with transporting the quantity of transportation fuel to the end user location by use of the selected distribution pathway. In another embodiment, the instant method further involves determination, by the controller, of the transportation fuel CI as a function, e.g. of 1) carbon emissions per unit energy associated with procuring the selected feedstock at the source, 2) carbon emissions per unit energy associated with transporting the feedstock from the source to the transportation fuel production facility by use of the selected transportation pathway, 3) carbon emissions per unit energy associated with processing the feedstock into transportation fuel transportation fuel together with operating the one or more transportation fuel production processes, and 4) carbon emissions per unit energy associated with transporting the quantity of transportation fuel to the end user location by use of the selected distribution pathway. The method may further include verifying, by the controller, that the CI of the transportation fuel remains below the CI threshold for the transportation fuel to be provided to the end user location; generating an identifying record that may include one or more of 1) the CI of the transportation fuel, or 2) the CI associated with or attributable to a selected feedstock, a transportation pathway, one or more transportation fuel production processes, and/or a distribution pathway associated with the transportation fuel; and outputting the transportation fuel through the selected distribution pathway as a low CI transportation fuel.

In certain aspects, the transportation fuel production facility of the disclosed method is a refinery, and one of the two or more feedstocks is selected from a hydrocarbon source. Embodiments of the method may further comprise processing the feedstock from the hydrocarbon source into additional transportation fuel while further operating the selected one or more transportation fuel production processes. Additionally, the transportation fuel may consist of traditional diesel, renewable diesel or ultra-low CI diesel fuel, where the traditional diesel, renewable diesel or ultra-low CI diesel fuel is produced or partially produced by processing the resulting oil. A biodiesel or renewable diesel may, in certain aspects, be used as an additive to traditional, petroleum based diesel, at a concentration of about 1% to about 25% of the petroleum diesel, including about 2%, about 5% and about 20% of the petroleum diesel. In further embodiments, pre-processing in accordance with the claimed method additionally and advantageously results in the production of sustainable meal that may be incorporated in or formulated as foodstuffs including feed products for livestock. The transportation fuel may, in certain aspects, be selected from one or more of a) a carbon-neutral transportation fuel, or b) a fuel that is substantially free from carbon in relation to the manufacturing and transporting of the transportation fuel.

In certain embodiments, one or more of the transportation pathway and the distribution pathway uses one or more alternative/renewable energy sources selected from of 1) electric power generated via wind energy, 2) electric power generated from solar energy, 3) electric power generated by a hydroelectric generator, which may include one or more microhydropower generators or systems, 4) electric power generated by a geothermal power generator, including dry steam powered and/or flash steam powered generators or systems, or 5) renewable diesel, including but not limited to any biodiesel that satisfies the ASTM D975 specification for such fuels. In related aspects, the transportation pathway may be chosen from the group consisting of rail, vehicle and barge, and may optionally include two or more of these pathways. The electricity generated by a renewable source for use in certain aspects of the disclosed technology may include electricity that is generated by one or more of 1) a wind turbine, 2) a solar array, 3) a geothermal power generator, 4) a hydroelectric generator, or 5) a stationary fuel cell power system. For instance, hybrid systems consisting of, e.g. stand-alone wind and solar electric systems may be utilized.

In an embodiment, the carbon intensity associated with procuring the selected feedstock at the source includes a carbon intensity of the selected feedstock and a carbon intensity for providing the feedstock at the source. In other aspects directed to the energetics of the present technology, the function of carbon emissions per unit energy associated with procuring the selected feedstock at the source may include carbon emissions per unit energy of the selected feedstock, as well as carbon emissions per unit energy for providing the feedstock at the source, including but not limited to a regenerative agricultural operation such as a regenerative farming operation, a regenerative grazing operation, a regenerative aquaculture operation and/or a regenerative ranching operation. In certain embodiments, the transportation fuel production facility is co-located with or proximal to one or more of the one or more sources, including but not limited to one or more of the foregoing regenerative agricultural operations.

Some aspects of the present disclosure relate to a system for operating a transportation fuel production facility for the distribution of a low carbon intensity (CI) transportation fuel that is produced as described herein and obtained through one or more targeted reductions of carbon emissions (CE). For instance, a controller may be implemented to control one or more of transportation fuel production processes as expressly or inherently described herein to be operated at one or more transportation fuel production facilities. A controller may, in some aspects, include one or more processors and memory storing instructions, such that the instructions, when executed by the one or more processors, are capable of a) determining a feedstock CI for each of one or more available feedstock(s) from one or more available feedstock sources that are supplied to the one or more transportation fuel production facility or facilities from one or more available feedstock transportation pathways, the one or more available feedstock sources including a regenerative agricultural operation as described herein and including, e.g. a regenerative farm, and the one or more available feedstock(s) including, in certain aspects, a crop from the regenerative farm, b) determining a feedstock transportation CI for each of the one or more available feedstock(s) as well as the one or more available feedstock transportation pathways associated therewith based on 1) a volume of a feedstock transportation pathway, 2) the type of fuel utilized by the feedstock transportation pathway, and 3) the distance required for travelling to the one or more transportation fuel production facility/facilities. Additionally, the controller may include wireless and/or cloud based processing and storage capabilities.

The memory of the disclosed system may, in certain embodiments, receive one or more instructions to 1) determine actual feedstock CI for the selected one or more available feedstock, and/or 2) determine actual feedstock transportation CI for the selected one or more feedstock transportation pathways, in response to the determined reception of the selected one or more available feedstock at the transportation fuel production facility, and may further receive instructions to select one or more different transportation fuel production processes, one or more different utilities, and one or more different transportation fuel distribution pathways to maintain total CI in response to a determination of an increase of the combined CI of the actual feedstock CI and actual feedstock transportation CI in relation to the combination of the determined feedstock CI and the determined feedstock transportation CI. In additional aspects, the memory has further instructions to a) determine actual transportation fuel production process CI for the selected one or more transportation fuel production processes, and b) determine actual utility CI for the selected one or more utilities, in response to the determination of the completion of the selected transportation fuel production processes.

Additionally, and in response to a determination of an increase of the combined CI of the actual transportation fuel production process CI and actual utility CI in relation to the combination of the determined transportation fuel production process CI and determined utilities CI, the memory may, in particular embodiments, select one or more different transportation fuel distribution pathways to maintain total CI. The memory may, in still further aspects and responsive to the completion of the transportation fuel distribution pathways, have instructions to determine the actual CI for 1) the selected one or more available feedstock, 2) a completed one or more feedstock transportation pathway(s), 3) a completed one or more transportation fuel production process or processes, 4) one or more utilities used to operate the completed transportation fuel production processes, and 5) a completed one or more transportation fuel distribution pathway. These determination may be based on, in certain embodiments, one or more of 1) an actual transportation fuel yield, 2) an actual transportation fuel volume, 3) the actual CI for the completed one or more feedstock transportation pathways, 4) the actual CI for the completed one or more transportation fuel production processes, 5) the actual CI for the one or more utilities used to operate the completed one or more transportation fuel production processes, and 6) the actual CI for the completed one or more transportation fuel distribution pathways, and transmitting an audit report including the actual CI for each selection and for the actual total CI.

In additional embodiments, a determination of the transportation fuel production process CI for each of one or more transportation fuel production processes may be performed based on 1) one or more available transportation fuel production processes available at the one or more transportation fuel production facility or facilities, where one of the one or more available transportation fuel production processes includes the capacity for pre-processing the feedstock via the crushing of crop segregates to form an oil capable of being utilized as and/or formulated in a transportation fuel, 2) a type of feedstock of the one or more available feedstock(s), 3) a type of oil formed during the pre-processing of the feedstock(s), and 4) a yield of each of the one or more available transportation fuel production processes. In related aspects, a determination of the utilities CI for each of one or more utilities is carried out based on 1) a type of utility to be used during a transportation fuel production process, and 2) the utilities' source. Further embodiments include determining a transportation fuel distribution CI for each available transportation distribution pathways on the basis of the volume and type of transportation fuel distribution pathway, the fuel type that is utilized by the transportation fuel distribution pathway, and the requisite travel distance associated with the delivery of the transportation fuel.

The system may, in additional aspects, involve the determination of a set or sets of combinations for optimizing the system that includes 1) one or more available feedstock(s), 2) one or more available feedstock transportation pathways, 3) one or more transportation fuel production processes of one or more transportation fuel production facility, 4) one or more utilities, and 5) one or more available transportation fuel distribution pathways. Accordingly, in related aspects a determination for the total CI for each of the one or more combinations may be performed based on 1) a volume of the one or more available feedstock, 2) a yield from the one or more transportation fuel production processes, 3) the determined feedstock CI, 4) the determined feedstock transportation CI, 5) the determined transportation fuel production process CI, 6) the determined utilities CI, and 7) the determined transportation fuel distribution CI. Following the foregoing determinations, a final selection from the set of combinations may be made that advantageously includes a total CI less than or equal to a "threshold CI," which is defined herein as an upper limit of CI in providing transportation fuel to an end user location that qualifies the transportation fuel as a low CI transportation fuel.

The CI of the transportation fuel may be, in accordance with certain system embodiments, a function of the total carbon emissions per unit energy of the transportation fuel based on the selectable set of combinations, where the final selection of combinations includes one or more of 1) a selected one or more available feedstock, 2) a selected one or more feedstock transportation pathways, 3) a selected one or more transportation fuel production processes of one or more transportation fuel production facilities, 4) a selected one or more utilities, and 5) a selected one or more transportation fuel distribution pathways. Following the final selection, in further aspects a feedstock request may be transmitted based on the (one or more) available feedstock and available feedstock transportation pathways that are chosen, and the controller may initiate the selected one or more transportation fuel production processes of the one or more transportation fuel production processes, and the selected one or more utilities to operate the selected one or more transportation fuel production processes for transforming the selected one or more available feedstock(s) to transportation fuel in response to a determined reception of the selected one or more available feedstock(s) at the one or more transportation fuel production facilities.

In related aspects, and in response to the determination of the completion of the selected one or more transportation fuel production processes, a delivery request of the transportation fuel may be transmitted via the selected one or more transportation fuel distribution pathways. Moreover, the determination of the final selection from the set of combinations may be based on, in further aspects, one or more of 1) the total CI, 2) the time of availability of each of the available feedstock(s), 3) a time for delivery to the transportation fuel production facility by each of the feedstock transportation pathway or pathways, 4) a time to process one or more available feedstock(s) utilizing each of the transportation fuel production processes, and 5) a length of time to deliver (from the transportation fuel production facility to an end user) the transportation fuel by each of the transportation fuel distribution pathways.

Additional aspects of the system may include the determination of the feedstock CI based on one or more of 1) a volume of each of the one or more available feedstock(s), 2) a type of feedstock of each of the one or more available feedstock(s), 3) a type of fuel utilized by equipment at the feedstock source or sources, 4) a type of fertilizer utilized for the feedstock(s), 5) a location of each of the one or more available feedstock(s), and 6) regenerative agricultural techniques, including but not limited to regenerative farming operations, that are utilized at the feedstock source, while still further embodiments include determining the total CI on the basis of feedstock storage CI, and where the memory has further instructions to determine the feedstock storage CI based on 1) a time each stored feedstock has been stored in each feedstock storage, and 2) a time and power associated with regulating the temperature of each of the one or more stored feedstock(s). Embodiments of the system further include the determination of the total CI based on a transportation fuel storage tank CI, and where the memory has additional instructions to determine the transportation fuel storage tank CI based on 1) a time the transportation fuel will be stored in each of the one or more transportation fuel storage tanks, 2) a time and power associated with regulating the temperature of each of the transportation fuel storage tanks, and 3) an estimated volume associated with emissions attributable to each of the transportation fuel storage tanks. Further aspects include options for the transportation fuel production process to perform one or more of 1) providing electrical power for the transportation fuel plant through renewable sources selected from wind, solar, hydroelectric, geothermal, hydrogen and combinations thereof, 2) employing renewable fuels in boilers and fired heaters of the transportation fuel plant selected from one or more of renewable diesel and renewable natural gas, and 3) sequestering carbon dioxide ($CO_2$) that is produced during the transportation fuel production processes.

The present disclosure further provides for a controller capable of operating one or more transportation fuel production facilities for the distribution of low carbon intensity (CI) transportation fuel produced by such facilities and obtained through one or more targeted reductions of carbon emissions (CE) as described herein comprising a first input/output in signal communication with a procurement computing device configured to determine a selection of one or more available feedstock(s), a selection of one or more feedstock transportation pathways, a selection of one or more transportation fuel production processes at one or more transportation fuel production facilities, a selection of one or more utilities, and a selection of one or more transportation fuel distribution pathways based on 1) a determination of feedstock CI of one or more blends of the one or more available feedstock(s) based on the volume and the type of feedstock(s), and further based on a CI associated with procuring a feedstock, at least one of which consists of a crop from a regenerative agricultural operation such as a regenerative farm, 2) a determination of feedstock transportation CI of one or more feedstock transportation pathways based on the delivery distance and the feedstock transportation pathway fuel type, 3) a determination of the transportation fuel production process CI of one or more transportation fuel production processes at one or more transportation fuel production facilities based on the type of transportation fuel production process, the volume and type of feedstock, and the length of time of the transportation fuel production process, where at least one of the transportation fuel production processes includes the pre-processing of a feedstock, via crushing of crop segregates, to form an oil for further processing, 3) a determination of the utility CI of one or more utilities based on the type of utility utilized to operate the transportation fuel production processes and the travel distance of the utility/utilities to the transportation fuel production processes, 4) a determination of transportation fuel distribution CI of one or more transportation fuel distribution pathways based on delivery distance and fuel type of a transportation fuel distribution pathway, and 5) a determination of one or more total CIs that are less than the threshold CI, where the total CIs are based on varying combinations of the CI determinations. In still further aspects and responsive to the selection of one or more available feedstock(s), the selection of one or more feedstock transportation pathways, the selection of one or more transportation fuel production processes at one or more transportation fuel production processes, the selection of one or more utilities, and the selection of one or more transportation fuel distribution pathways, the controller may transmit a feedstock request to the procurement computing device that includes the selection of the one or more available feedstock(s) and the selection of the one or more feedstock transportation pathways.

Additionally, the controller may consist of a second input/output in signal communication with a transportation fuel production facility controller for controlling one or more various transportation fuel production processes to be operated at the one or more transportation fuel production facility or facilities, where the controller is configured to 1) determine actual feedstock CI and actual feedstock transportation CI in response to a determined reception of the selected available feedstock at the transportation fuel production facility, 2) determine one or more of a new selection of one or more transportation fuel production processes, a new selection of one or more utilities, and a new selection of one or more transportation fuel distribution pathways to maintain total CI in response to a determination that the actual feedstock CI and actual feedstock transportation CI has increased in relation to the determined feedstock CI and determined feedstock transportation CI, and 3) initiate, at the transportation fuel production facility controller, the selected transportation fuel production processes at the transportation fuel production facilities and the selected utilities to operate the selected transportation fuel production processes at the transportation fuel production facilities for transforming the selected available feedstock(s) to transportation fuel.

The controller may, in additional aspects, consist of a third input/output in signal communication with a distribution computing device that is configured to 1) determine an actual transportation fuel production process CI and an actual utility CI in response to determination of completion of the selected one or more transportation fuel production processes at the selected one or more transportation fuel production facilities, 2) determine one or more new selections of one or more transportation fuel distribution pathways in response to a determination that the actual transportation fuel production process CI and actual utility CI has increased in relation to the determined transportation fuel production process CI and determined utility CI, and 3) transmit a delivery request of the transportation fuel via the selection of the transportation fuel distribution pathways to the distribution computing device. The transportation fuel production processes associated with the controller may, in some aspects, include offsetting practices that may include transportation fuel production processes to 1) provide electrical power for the one or more transportation fuel production facilities through renewable sources, the renewable sources comprising wind, solar, hydroelectric, geothermal, or hydrogen fuel cells, 2) employ renewable fuels selected from renewable diesel and/or renewable natural gas in boilers and fired heaters of the transportation fuel production facility, and 3) sequester $CO_2$ produced during the transportation fuel production process or processes. Embodiments of the controller may, in additional aspects, relate to the sequestration of carbon monoxide and/or carbon dioxide produced during the one or more transportation fuel production processes involved in the production of low intensity hydrogen.

Additional advantages of the disclosed aspects and embodiments are further discussed in detail herein. It is to be understood, however that both the foregoing information and the following detailed description provide merely illustrative examples of various aspects and embodiments, and are intended to provide an overview or framework for understanding the nature and character of the claimed aspects and embodiments. Accordingly, these and other objects, along with advantages and features of the present disclosure, will become apparent through reference to the following description and the accompanying drawings. Furthermore, it is to be understood that the features of the various embodiments described herein are not mutually exclusive and may exist in various combinations and permutations.

BRIEF DESCRIPTION OF DRAWINGS

The disclosed aspects, features and advantages of the disclosure will become better understood with regard to the following descriptions, examples, claims, and accompanying drawings. Applicant notes, however, that the drawings illustrate certain embodiments of the disclosure and should not be considered limiting with regards to the breadth and scope of the disclosure.

DETAILED DESCRIPTION

Figure 1:
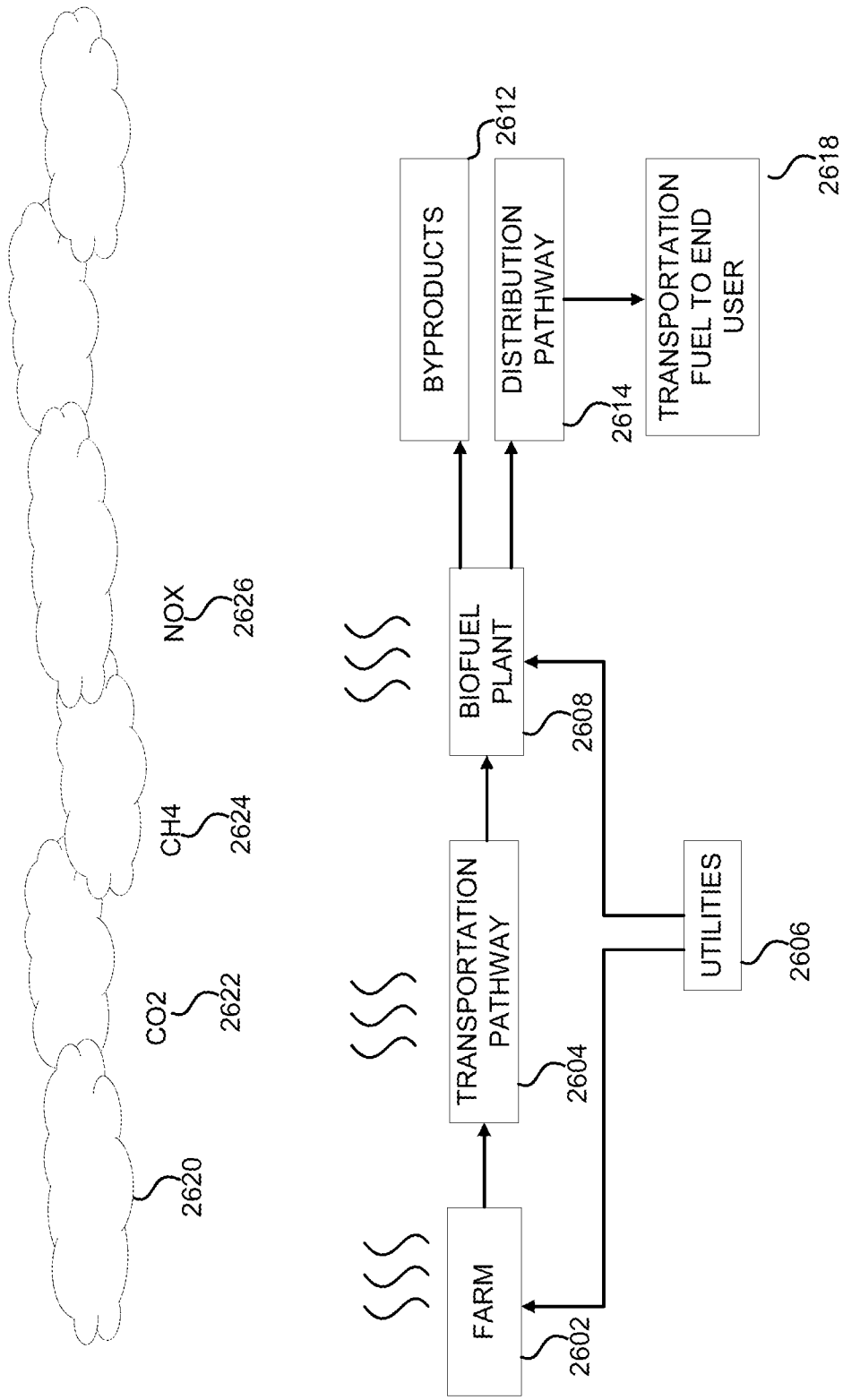
FIG. 1 is a diagram illustrating one or more embodiments that reduce carbon intensity using aspects of regenerative farming in the production and delivery of transportation fuel in accordance with one or more embodiments of the present disclosure.

The present disclosure provides embodiment of systems and methods related to systems and methods for the procurement, production, refinement and/or transformation of low carbon intensity transportation fuels, including low carbon intensity biodiesel, renewable diesel, low carbon intensity ethanol, and low carbon intensity hydrogen, that may be beneficially commercialized directly to consumers. In further aspects, the systems and methods of the present disclosure advantageously generate low carbon intensity comestibles, including sustainably-sourced meal and/or feed, and additional by-products to further reduce the carbon intensity associated with the disclosed technology.

In one or more embodiments, systems and methods for providing a low carbon intensity (CI) transportation fuel or transportation fuel additive, such as biodiesel, renewable diesel, and bioethanol, to an end user such as a consumer or a commercial customer are disclosed. The disclosed systems and methods are beneficially associated with more sustainable and less carbon-intensive processes than traditional petrochemical refinery processes and operations such as distilling, cracking, treating, separating and blending for producing carbonaceous, liquid transportation fuels, as well as commercializable by-products such as lubricants, waxes and heating oils. In addition, and similarly to fuels produced via traditional petrochemical refinement, the transportation fuels produced in accordance with the present disclosure may be transported through various distribution pathways to retail outlets for purchase by end user customers, as well as to commercial users for use in industrial processes.

The present disclosure is further directed to systems and methods for the production of low carbon intensity biofuels, bio-based fuels, and biofuel additives, such as biodiesel, renewable diesel, and bioethanol, that further accommodate the production of sustainable feeds, meals and related agricultural products derivable from regenerative farming. In one or more embodiments, systems and methods for providing a low carbon intensity (CI) biodiesel and/or renewable diesel to an end user are provided. As used herein, "regenerative farming" may refer to any agricultural operation utilizing or capable of utilizing carbon reduction and/or carbon sequestration for beneficially enhancing one or more of soil fitness, overall crop yield, water resilience, and/or nutrient concentration associated with the regenerative farming operation. Further, regenerative farming may include sustainable farming and/or agricultural techniques. As used herein, a "regenerative farm" may refer to a farm or location utilizing and/or employing regenerative and/or sustainable farming and/or agricultural techniques. For instance, and as would be appreciated by those of skill in the relevant art, in embodiments regenerative farming operations may advantageously reduce the CI associated with one or more transportation fuel processes disclosed herein by enhancing the levels of organic matter and mineral particles in the soil. The increased presence of these materials may subsequently enhance the concentration and/or activity of one or more of earthworms, lithotrophs, chemoautotrophs and/or additional soil-based organisms, which are in turn capable of imparting at least some of the foregoing soil and water benefits in the absence or reduction of one or more traditional farming techniques including but not limited to tilling, traditional fertilizing, watering, herbicide and/or pesticide treatment strategies.

The feedstocks selected for the production of transportation fuels in accordance with the present disclosure, where the feedstocks may be selected from one or more of soybean, corn, wheat, sugarcane, rapeseed, canola, mustard, sunflower, safflower, castor bean, jatropha and oilseed crops such as lesquerella and pennycress, have an initial or inherent carbon intensity, which is expressed as grams of carbon dioxide per unit energy and/or as a function of carbon emissions per unit energy. The associated initial or inherent carbon intensity represents the carbon emissions that would result if the feedstock—in its natural state absent any pre- or post-processing—were to be combusted completely, e.g., based on the complete combustion of the hydrocarbons to carbon dioxide ($CO_2$) and water based on stoichiometric combustion as would be understood by those skilled in the art. However, the procurement of agricultural feedstocks, the refinement of feedstocks into transportation fuels and fuel additives, and the distribution of those transportation fuels to the consumers and commercial entities represents myriad stages capable of increasing (or, in accordance with embodiments of the instant disclosure, decreasing) the carbon intensity of the resulting transportation fuel and/or fuel additive.

The production of biofuels and biofuel additives using the processes and methodologies known to the skilled artisan are often associated with the disadvantageous and disproportionate production of carbonaceous and/or thermal waste. For instance, the inherent carbon intensity (CI) of a crop feedstock may often be the largest CI contributor to the overall transportation fuel production process. Accordingly, the CI associated with the resulting transportation fuel or fuel additive is necessarily and unavoidably increased if carbon emissions (which may be expressed as grams of $CO_2$ equivalent per unit energy) are not beneficially mitigated using techniques and processes such as the regenerative agricultural processes of the present disclosure. For example, the determined grams of carbon dioxide equivalent per unit energy evolved as a result of the activity is added to the initial or inherent carbon intensity of the material, e.g., one or more crop feedstocks, that is the subject of the activity. Conversely, if activities that sequester carbon or mitigate the release of carbon emissions are employed, e.g. regenerative agricultural techniques such as regenerative farming, the resulting carbon emissions are more likely to be negative or zero such that the carbon intensity of the transportation fuel is advantageously reduced as a result of the activity, with further benefit afforded by the production of meal, feed or further consumables depending on the type of regenerative agricultural process employed.

Renewable energy is generally produced and distributed directly to consumers and commercial users through dedicated channels. The consumer and commercial users of renewable energy are often forced to make special accommodations, including but not limited to renewable energy infrastructure purchases and/or significant travel to distribution points, such that the use of renewable energy is sufficiently beneficial. In addition, energy sources associated with higher CI values, e.g., transportation fuels, are utilized in the construction and distribution of the renewable energy infrastructure or in the provision of renewable energy from its generation source to its procurement by end users. However, when the low carbon intensity of renewable energy can be beneficially paired with regenerative agricultural methods such as regenerative farming as contemplated by the present disclosure, any necessary use of higher carbon intensity energy sources can be partially or significantly offset.

In some embodiments disclosed herein, the systems and methods may provide for low carbon intensity transportation fuels produced through one or more targeted reductions of carbon emissions associated with various options for crop feedstock procurement, crop feedstock transportation, crop feedstock refinement, and fuel product/refined product/refined crop feedstock distribution pathways and channels associated with and/or supplemental to the regenerative agricultural processes and strategies described herein. In non-limiting embodiments, renewable energy sources, such as power generated from wind, solar, geothermal, and hydroelectric generators as well as additional, renewable feedstocks obtained from biomass sources (e.g., additional plant crops/waste and/or animal waste), may be combined with the regenerative farming methods of the present technology for beneficially reducing carbon emissions. In addition to regenerative farming, additional regenerative agricultural techniques, e.g. regenerative grazing, regenerative aquaculture and/or regenerative ranching, may be partially or wholly utilized in tandem and/or in combination with renewable energy sources and/or additional, renewable feedstocks for optimally reducing carbon emissions. For instance, aspects of regenerative ranching associated with animal waste that may be implemented as fertilizer in regenerative farming processes may be used to the extent that such a combinatorial regenerative agriculture strategy is capable of reducing or further reducing carbon waste and/or capable of enhancing carbon sequestration. The use of one or more regenerative agricultural techniques and/or one or more renewable energy sources are non-limiting in accordance with the present disclosure to the extent that the requirement of the formation of one or more oils or further compositions, e.g. bioalcohols such as bioethanol, capable of being utilized or incorporated into transportation fuels is satisfied.

As a result of the systems and methods disclosed herein, the transportation fuels produced therefrom have a lower carbon intensity due to the low carbon intensity regenerative agricultural processes and alternative energy sources integrated into the product transportation fuels during, e.g., crop feedstock selection, transportation, processing and product distribution. The integration of alternative, renewable energy sources, which may be co-located geographically with regenerative agriculture operations and sites as disclosed herein, reduces additional carbon intensity associated with transporting biofuels and/or biofuel additives directly to consumers and commercial users. In non-limiting beneficial aspects, the consumer purchaser of these lower carbon intensity transportation fuels and other refined products receives conventional transportation fuels available with carbon intensities that have been partially or significantly offset by the regenerative agriculture based processing steps that use the lower carbon intensities in combination with alternative, renewable energies, such that lower carbon intensities are verifiably integrated into the lower carbon intensity (CI) conventional transportation fuel. Additionally, the low carbon conventional transportation fuels produced in accordance with the instant disclosure may be easily purchased from traditional retail outlets, e.g., convenience stores, without unduly inconveniencing consumers needing to purchase special vehicles and/or equipment, e.g., electric vehicles or modified combustible engines, to benefit from the low carbon intensity energy afforded by the combination of regenerative agricultural/renewable energy solutions disclosed herein.

In accordance with certain aspects of the instant disclosure, FIG. 1 illustrates a more holistic approach to reducing carbon intensity, as well as limiting emission of certain chemicals into the atmosphere 2620. The introduction of chemicals into the atmosphere 2620 as a result of biofuel, renewable diesel, biodiesel and/or ethanol production, as well as an ethanol blending operation with refined transportation fuel, may include carbon dioxide ($CO_2$) 2622, methane ($CH_4$) 2624, nitrogen oxides ($NO_x$) 2626, and/or other chemicals as disclosed herein and as will be understood by the skilled artisan. A more holistic approach to carbon intensity (CI) as contemplated in the instant disclosure encompasses a reduction in the CI of each process or stage in a biofuel production system and/or operation (including any associated indirect and direct processes or stages), as well as a CI reduction in the overall carbon intensity of a biofuel to a consumer or commercial customer location 2618 (e.g., an ultra-low carbon intensity biofuel, renewable diesel, biodiesel and/or fuel additive such as bioethanol capable of reducing the carbon intensity of a transportation fuel). As such, the carbon intensity associated with a regenerative farming operation consisting of one or more crop feedstock sources 2602 (e.g., an agricultural site, farm, agricultural waste facility, or other source of regenerative agricultural feedstock) may be strategically targeted for carbon intensity (CI) reductions (e.g., an indirect process or stage with regards to the biofuel plant 2608) in accordance with the present disclosure.

Accordingly, carbon intensity reductions may be achieved through the selection of different CI reducing methods, including but not limited to the use of low carbon intensity utilities 2606 or the use of low carbon intensity fertilizer and/or pesticides, for producing crop feedstock at the crop feedstock source 2602. As used herein and described in the foregoing, a "crop feedstock" may refer to a variety of different feedstocks, including but not limited to soybean, corn, wheat, sugarcane, rapeseed, canola, mustard, sunflower, safflower, castor bean, jatropha, lesquerella, pennycress, rice, other grains, fruits, vegetables, other vegetation, other organic matter and/or other organic waste capable of producing one or more oils or further compositions, e.g. bioalcohols such as bioethanol, that may be utilized as or incorporated into transportation fuels.

The carbon intensity (CI) associated with crop feedstock transportation pathways 2604 (including commercial trucking, commercial vehicle, rail and/or marine transportation) may also be strategically targeted for CI reduction at one or more points, such as at an indirect process or stage in relation to biofuel plant 2608. In addition, the carbon intensity at the biofuel plant 2608 may be targeted for potential CI reduction, e.g., using renewable and/or low carbon intensity utilities 2606, through the use of carbon capture/sequestration, and/or by biofuel production process improvements. Low carbon intensity utilities 2606 in accordance with the present disclosure may be co-located at, proximate with, and/or dedicated to the biofuel plant 2608, including off-grid utilities, wherein the low carbon intensity utilities 2606 provide dedicated power solely to the biofuel plant 2608. The carbon intensity for other processes or stages may be considered for carbon intensity reduction, such as biofuel distribution pathways 2614 for transport of biofuel to an end user 2618 (for indirect CI reduction) and/or through further use, processing or blending of biofuel processing byproducts 2612 (including but not limited to crop feedstock/plant components, fluids and/or oils, and/or other byproducts) produced at the biofuel plant 2608. The carbon intensity for other processes or stages of a regenerative agriculture based transportation fuel operation, as described above, may be targeted for CI reduction, including but not limited to a blended transportation fuel distribution pathway for the transport of a biofuel-based transportation fuel to an end user location 2618, through indirect CI reduction.

Figure 2:
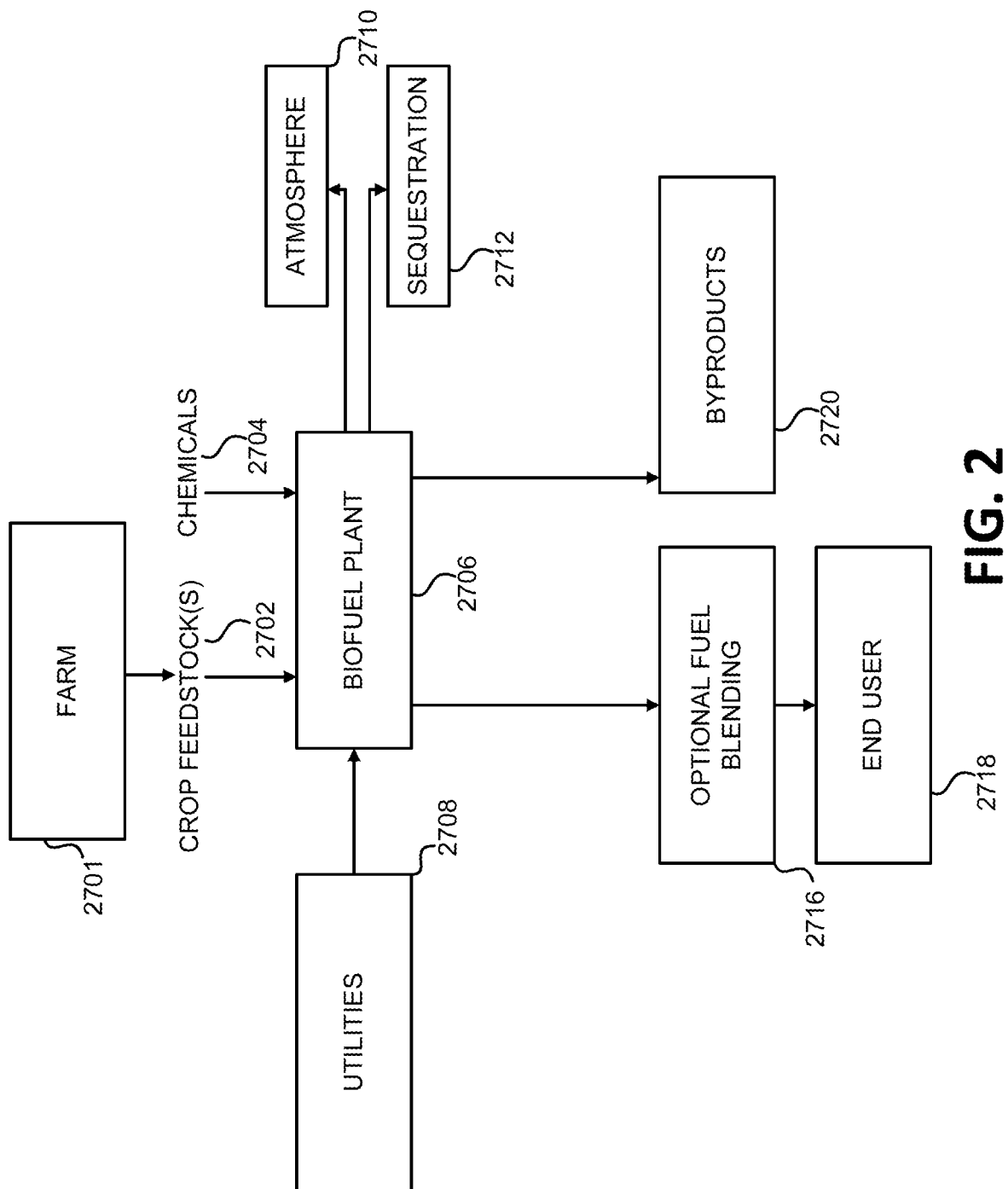
FIG. 2 is a simplified diagram illustrating a novel implementation of a low carbon intensity biofuel strategy employed during the production of biofuel and related compositions as well as the distribution and delivery of the resulting low carbon intensity biofuel, according to certain embodiments of the present disclosure.

FIG. 2 is a simplified diagram that illustrates a novel implementation of a low carbon intensity biofuel strategy in which lower carbon energy is introduced and used during the acquisition, transportation and processing of crop feedstock(s) procured from a regenerative agriculture operation such as a regenerative farm 2701, as well as the ultimate transport and distribution to an end user 2718 as a low carbon intensity (CI) transportation fuel. In accordance with certain aspects of FIG. 2, the implementation of low carbon energy sources or utilities 2708 generates biofuel capable of being directly or indirectly supplied as a low carbon intensity liquid transportation fuel and characterized by diminished CI in accordance with embodiments of the disclosure. Biofuels consisting of lower carbon intensity liquid transportation fuels, which are verifiably lower in carbon emissions, may subsequently be transported and delivered to distribution points, including an end user 2718 such as a consumer or commercial user, including a retail outlet and/or convenience store. In aspects where, e.g. a convenience store is the ultimate commercial destination, the consumer is advantageously not required to purchase or utilize any special equipment such as an alternative fuel, electric or natural gas-powered vehicle, to benefit from low carbon energy sources that may distally located from the consumer, because such low carbon energy sources have been directly used as a liquid transportation fuel and/or integrated into purchased liquid transportation fuels, e.g., in the form of one or more of renewable diesel, biodiesel, biogasoline, mixed biogasoline for small engines such as 2-cycle gasoline engines, and bioalcohol such as bioethanol.

FIG. 2 further illustrates a novel utilization strategy for low CI in which lower carbon intensity energy (e.g., from utilities 2708) is integrated into the procurement and delivery of crop feedstock(s) 2702 and chemicals 2704 such as catalysts, acids and/or alcohols to enhance production of the resulting biofuels such as renewable diesel and/or bio-based fuel additives, e.g., at a biofuel (or biofuel additive) plant 2706. Low carbon intensity utilities 2708, including wind farms, solar arrays, hydroelectric power sources, geothermal power plants/facilities, and/or stationary fuel cell power systems) may be strategically integrated into the regenerative farming based strategy wherein a regenerative farm 2701 produces crop feedstocks 2702 capable of decreasing overall CI of biofuel and/or biofuel or biofuel additive to be blended with refined transportation fuels at an optional fuel blending site 2716. However, these low CI blended transportation fuels are capable of supporting the existing renewable energy infrastructure and are transported to locations accessible to consumers and other end users 2718. For example, low carbon intensity blended transportation fuels and other refined products provided through a regenerative agriculture based biofuel strategy may be used to at least partially construct and provide a renewable fuel infrastructure, including but not limited to electric-powered vehicles, natural gas-powered vehicles, dedicated charging/refueling stations, that beneficially allows consumers and commercial end users to take advantage of the resulting renewable energy. Further, low carbon intensity fuels consisting of biofuel and/or biofuel additives such as bioethanol produced by biofuel plant 2706 may be necessary to partially, if not fully, produce renewable energy, such as renewable diesel and low CI blended fuels such as biodiesel and biodiesel supplemented "traditional" diesel fuel and to transport renewable energy to distribution access points available to consumers and other end users 2718. Accordingly, low CI biofuels and blended transportation fuels produced through the integration of regenerative farm 2701, renewable energy such as renewable utilities 2708 and/or biofuel plant 2706 improvement processes. These improvement processes may include but are certainly not limited to carbon capture and sequestration 2712, which may encompass the same, similar or different carbon capture and sequestration strategies as those employed in the regenerative farm 2701, are preferred in comparison with atmospheric release 2710 of potentially deleterious waste and byproducts.

Alternatively, and in lieu of the atmospheric release 2710 of potentially harmful byproducts, the resulting CI of the overall regenerative farming based transportation fuel process may be beneficially decreased through the re-use (if possible) of byproducts 2720 produced at the biofuel plant 2706. For instance, excess crop feedstock components or subcomponents such as unused plant parts or fluids may be aggregated and further processed, e.g. to produce additional quantities of plant oil for ultimate use in biofuels, biofuel additives and/or other transportation fuels. In addition, the byproducts 2720 may be used to produce bio-based commodities and/or specialty polymers in accordance with processes known to the skilled artisan. Finally, additional foodstuffs may be produced downstream of the meals and feeds produced, e.g. from pre-processing, e.g. an initial crushing or grinding, of crop feedstocks to produce an initial plant oil fraction for use in the production of biofuel and related fuels/components at biofuel plant 2706. The utilization and production of byproducts 2720 may advantageously offset or significantly reduce the CI associated with biofuel production.

Figure 3:
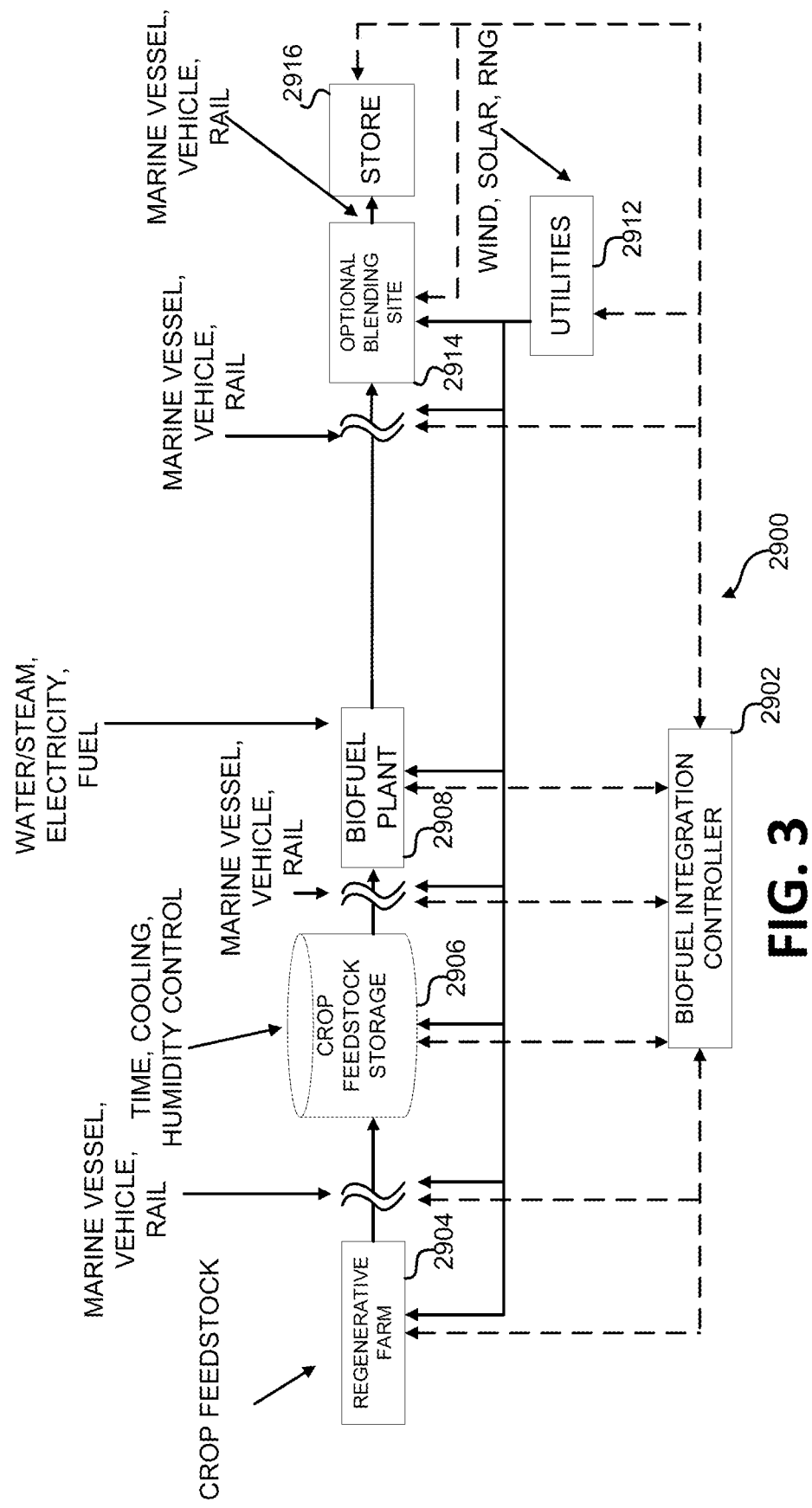
FIG. 3 is a block diagram illustrating a system for managing low carbon intensity biofuel production according to embodiments of the disclosure.

FIG. 3 is a block diagram illustrating a system 2900 for controlling and managing low carbon intensity (CI) biofuel production in accordance with embodiments of the instant disclosure. The system 2900 may include a biofuel integration controller 2902 connected to one or more controllers, sensors, and/or computing devices, included cloud based devices, utilized throughout a biofuel production process or operation for controlling and optimizing biofuel production. For instance, in embodiments biofuel integration controller 2902 may be in operable connection with a controller at regenerative farming operation 2904 or to a database storing information regarding the crop feedstock source derived from the regenerative farming operation 2904. Accordingly, biofuel integration controller 2902 may obtain various data points, information, etc., or information in relation to different or supplemental crop feedstocks available at regenerative farm 2904.

The biofuel integration controller 2902 may select one or more of the available crop feedstock(s) for use in biofuel and/or biofuel additive production, based on the available data or information, and may select supplemental crop feedstock(s) at any point prior to, during or after the manipulation of crop feedstock(s) that were previously processed into biofuel available components, e.g. oil, and/or feeds, meals or additional foodstuffs. The data points available to biofuel integration controller 2902 may include the fertilizer and/or pesticide types used (including conventional versus low CI fertilizer and conventional versus low CI pesticide), the type of crop feedstock(s) utilized and/or potentially available for processing and incorporation into the system 2900, the distance of the crop feedstock(s) procured from regenerative farm 2904 to biofuel plant 2908 (which may be co-located, located proximate to or nearby regenerative farm 2904), and the type of fuel and utilities used by the equipment utilized at regenerative farm 2904, i.e., alternative/renewable fuel(s), fossil fuel(s), etc.

The biofuel integration controller 2902 may, in some aspects, connect to controllers, sensors, and one or more databases and/or computing devices, including cloud based devices related to a transportation pathway based on crop feedstock supplied via a regenerative farm 2904. Accordingly, the biofuel integration controller 2902 may obtain various data points, information, etc., for different available crop feedstock transportation pathways (including but not limited to distance between regenerative farm 2904 and crop feedstock storage 2906 and/or biofuel plant 2908, the crop feedstock transportation pathway utilized, the type of fuel (renewable, fossil, etc.) utilized by the crop feedstock transportation pathway, and/or the volume associated with the crop feedstock transportation pathway). Biofuel integration controller 2902 may select one or more of the available crop feedstock transportation pathways for biofuel, based on any available and processable data points, information, etc.

Moreover, biofuel integration controller 2902 may be operably connected to controllers, sensors, and/or computing devices, including cloud based devices, associated with crop feedstock storage 2906, which may be positioned at various points between regenerative farm 2904, biofuel plant 2908, optional blending site 2914, and a distribution point or terminal, for instance a convenience store 2916. For example, crop feedstock storage 2906 may be located on-site at biofuel plant 2908. Biofuel integration controller 2902 may procure data points and/or information related to the crop feedstock, biofuel, and/or blended biofuel at myriad points within the system.

The biofuel integration controller 2902 may control a biofuel plant 2908 and/or connect to controllers, sensors, and/or computing devices operating at the biofuel plant 2908. The biofuel integration controller 2902 may obtain various data points or information in relation to different available fuel production processes of the biofuel plant 2908 and biofuel integration controller 2902 may select one or more of the available biofuel production processes for the biofuel and/or biofuel blended transportation fuel production, based on the available data and/or information. In certain embodiments, the biofuel integration controller 2902 may initiate or control particular biofuel production processes at biofuel plant 2908. For instance, upon the selection of a particular biofuel production process, biofuel integration controller 2902 can initiate the biofuel production process or transmit an initiation to a controller operably connected to biofuel plant 2908. The biofuel integration controller 2902 may further determine where to send or transport byproducts of biofuel plant 2908. For example, a byproduct may include feed. The feed may include a CI proportional to the CI of the produced biofuel and the volume of crop feedstock utilized at biofuel plant 2908. In a non-limiting example, biofuel integration controller 2902 may initiate transportation of the feed using, e.g. a marine vessel, vehicle (e.g., a commercial truck) and/or a rail system (i.e., a train) to an agricultural site for feeding animals, with a particular CI partially based on the feed's CI.

The biofuel integration controller 2902 may connect to a utility provider 2912 or controllers, sensors, and/or computing devices associated with a utility provider 2912. Utility provider 2912 may provide utilities for use in biofuel plant 2908, as well as at various other points throughout crop feedstock processing and/or biofuel production. The utility provider 2912 may be proximate to, nearby, or on site with the biofuel plant 2908 and may utilize one or more alternative/renewable energy resources. In particular embodiments, the utility provider 2912 may be off-grid and/or dedicated to biofuel plant 2908. For example, one or more of a solar panel farm, a wind turbine farm and/or a hydroelectric facility may be constructed on site or proximal to the biofuel plant 2908. In a non-limiting example, utility provider 2912 may provide and/or track utilities for use at biofuel feedstock source 2904, at each transportation/distribution pathway, at each processing location, storage location or tank (such as crop feedstock storage 2906), at an optional blending site 2914, and/or at other junctures or processes associated with biofuel production in accordance with the present disclosure. Accordingly, biofuel integration controller 2902 is capable of obtaining data and/or information attributable to any available utilities, as well as available utilities for biofuel production in accordance with the disclosed technology. Biofuel integration controller 2902 may then utilize the available data/information for selecting one or more utilities for biofuel production, such as utilities for use in the one or more selected biofuel production processes.

Biofuel integration controller 2902 may, in some embodiments, be operably connected to one or more controllers, sensors, databases and/or computing devices, including cloud based devices, related to a biofuel distribution pathway. In accordance with aspects of the disclosure, the biofuel integration controller 2902 may obtain various data points or information in relation to different available biofuel distribution pathways, and may subsequently select one or more of the available biofuel distribution pathways based on the available data points and/or information.

Biofuel integration controller 2902 may connect to an optional blending site 2914 or to controllers, sensors, and/or computing devices located at or in operably contact with optional blending site 2914, which may perform blending of biofuel product with traditional, hydrocarbon transportation fuel, as well as blending with one or more additional, separate biofuels and/or biofuel additives such as bioethanol. Biofuel integration controller 2902 may provide data regarding a produced biofuel or biofuel additive such as a bioalcohol to such components at optional blending site 2914. For instance, biofuel integration controller 2902 may connect to an optional blending site 2914 controller for initiation of shipment of the biofuel product to optional blending site 2914. Biofuel integration controller 2902 may also provide the CI of the biofuel product, as well as various other aspects of the biofuel production process, such as the CI and the type of crop feedstock utilized, the CI and the type of crop feedstock transportation utilized, the CI and the type(s) of biofuel processes utilized, the CI and the type of utilities utilized, the CI and the type of byproducts produced as well as locations to where the byproducts may be shipped, and/or the CI and the type of biofuel distribution utilized. The biofuel integration controller 2902 may also procure data points or information directed to the optional blending site, including but not limited to the amount of each component to be blended, the requisite power needed for blending, the type and duration of the blending operation, etc.

Biofuel integration controller 2902 may, in certain aspects, select one or more of the available optional blending processes for biofuel, including in instances where biofuel is blended with additional separate biofuels, blended with biofuel additives such as bioethanol and/or blended with refined transportation fuel, based on available data points and/or information. Biofuel integration controller 2902 may further initiate and/or control any available, selected blending processes. In a non-limiting example where one or more blending processes are selected, biofuel integration controller 2902 may initiate the blending processes and/or transmit an initiation prompt to a controller of optional blending site 2914. Additionally, biofuel integration controller 2902 may obtain the CI for any of additional biofuel(s), biofuel additives and/or refined transportation fuel that is to be blended with the produced biofuel at optional blending site 2914.

In some aspects, biofuel integration controller 2902 may connect to controllers, sensors, and/or computing devices at a distribution point or terminal, such as a convenience store 2916. For instance, biofuel integration controller 2902 may be configured or enabled to monitor or track fuel consumption for best anticipating fuel consumption and/or demand at the convenience store 2916. Based on that consumption and/or demand, biofuel integration controller 2902 may initiate biofuel production at biofuel plant 2908 and/or biofuel blending at optional blending site 2912. Further, based on consumption or demand for a particular type of biofuel (e.g., biofuel or blended biofuel associated with low or high CI), biofuel integration controller 2902 may select different aspects of biofuel production including the use of low CI methods at crop feedstock sources, carbon sequestration at regenerative farm 2904, at biofuel plant 2908 and/or at utilities 2912, the type and use of renewable utilities, etc. In a further example, the biofuel integration controller 2902 may beneficially monitor the cost or price of biofuel and/or biofuel blends. Based on the cost or price, as well as the cost or price of the crop feedstock(s), biofuel integration controller 2902 may initiate a biofuel production process.

Figure 4:
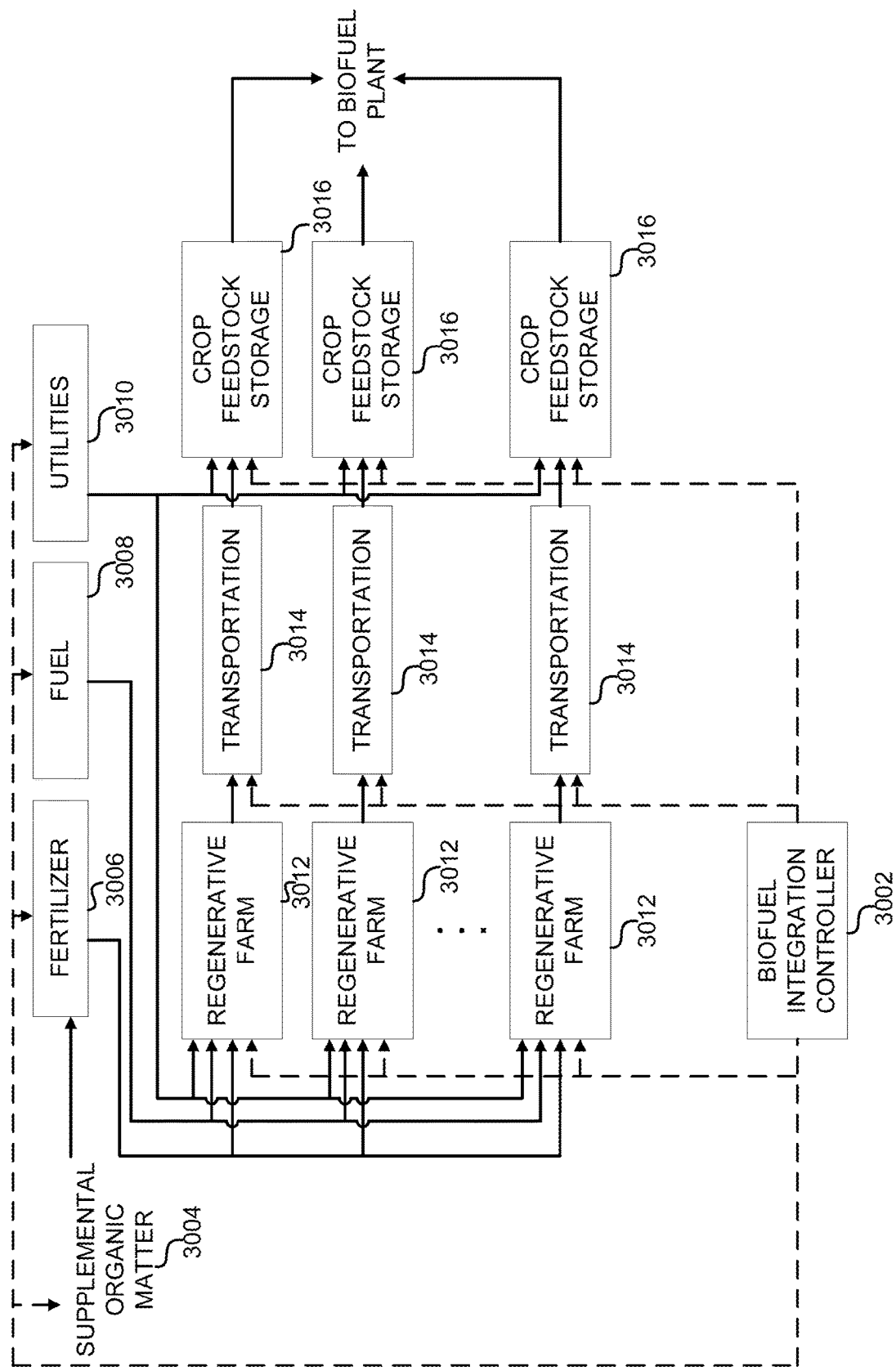
FIG. 4 is a block diagram illustrating a system for managing low carbon intensity biofuel production according to certain aspects of the present disclosure.

FIG. 4 is a block diagram illustrating a system for managing the low carbon intensity ethanol production according to an embodiment. In such embodiments, the system may utilize a biofuel integration controller 3002 and/or various other controllers or computer devices utilized throughout the ethanol production process. Such controllers may be utilized to select and initiate aspects of one or more of the biofuel production processes. The production of biofuel may comprise, in certain aspects of the present technology, a complimentary process in an overall scheme directed to the production of a transportation fuel and/or process, or a blended transportation fuel production and/or process. For instance, a particular CI may be set for a biofuel blended transportation fuel, and biofuel integration controller 3002 may then select and control biofuel production (or biofuel blended transportation fuel production) to lower the CI of the resulting biofuel or biofuel blended transportation fuel. Additionally, the biofuel integration controller 3002 may initiate biofuel production based on the lowest possible CI based on the options available for producing the fuel, such as available crop feedstocks, minimal production cost, maximal rate at which the biofuel can be produced, etc., and combinations thereof. In such embodiments, biofuel integration controller 3002 may consider a lower cost crop feedstock for a reduced cost CI biofuel based on one or more available utilities 3010, such as a solar panel farm, and additional options available at a specific time, where e.g., the solar panel farm may be operating and/or carbon capture or sequestration may or may not be available at the regenerative farm 3012. In another example, the biofuel integration controller 3002 may produce large quantities of biofuel characterized by a particular CI for a period of time and/or for a certain seasonal demand, weather conditions, etc. The resulting biofuel (or blended biofuel) may be stored until requested for a particular transportation fuel operation. In yet another example, the biofuel integration controller 3002 may factor in tax credits associated with commercial crop production and relevant agricultural exemptions.

As illustrated in FIG. 4, biofuel integration controller 3002 may connect to various and different stages of biofuel production processes, as well as to databases, computing devices and/or additional controllers or devices capable of providing data or information for each production stage. For example, the biofuel integration controller 3002 may connect to numerous regenerative farming operations 3012 capable of supplying various crop feedstock(s), and may further be in operable connection with one or more computing devices, controllers, etc., at the crop feedstock source(s) 3012 and/or in operable contact with a database that includes and is capable of conveying data relevant to the crop feedstock source(s) 3012. In certain aspects, biofuel integration controller 3002 may select one or more crop feedstock(s) based on numerous factors at each of the crop feedstock sources 3012. For example, the crop feedstock sources 3012 may utilize one or more of fertilizer 3006, fuel 3008, utilities 3010, including any combination thereof. In such examples, different crop feedstock sources 3012 may utilize different types of fertilizer 3006, fuel 3008, and/or utilities 3010. In a non-limiting example, one or more of the crop feedstock sources 3012 may consist of waste facilities capable of supplying organic waste including but not limited to plant based carbohydrates such as starches, simple sugars and/or fibers. Additionally, the crop feedstock(s) may be harvested or collected using farming equipment that optionally utilizes fuel 3008 and is located at one or more regenerative farms 3012. In related aspects, biofuel integration controller 3002 may consider fuel 3008 utilized in such capacities at one or more regenerative farms 3012, which may consist of low CI fuel, biofuel and other renewable fuel such as renewable diesel, biodiesel, biogasoline, aviation fuels including but not limited to jet fuel including any aviation turbine fuel that satisfies the ASTM D1655 standard, Jet A, Jet A-1, and Jet B fuels, aviation gasoline such as 100LL Avgas, aviation diesel, aviation kerosene such as QAV-1, marine fuel, engineered marine fuels, marine diesel oil, heavy fuel oil, low-sulfur fuel oil, marine gas oil, biokerosene, synthetic kerosene, blendable and/or pre-blended fuels for use in 2-cycle gas-powered engines, traditional fossil fuels, and one or more combinations thereof, and the CI associated with any one of or all of the utilized fuel(s) 3008. Additionally, biofuel integration controller 3002 may further be capable of incorporating utilities 3010 used at one or more crop feedstock sources of the one or more regenerative farms 3012, which may include renewable energy sources and/or traditional energy sources.

In some aspects, biofuel integration controller 3002 may select or control the type of transportation 3014 used for shipping crop feedstock(s) between the one or more crop feedstock sources of the one or more regenerative farms 3012 and one or more crop feedstock storage locations 3016 or directly to a biofuel plant. Biofuel integration controller 3002 may consider and select the type of transportation based on the distance that one or more types of transportation 3014, e.g., rail, marine and/or truck, may be required to travel for delivering the crop feedstock to crop feedstock storage 3016 or directly to biofuel plant 3020, which may include the amount of crop feedstock to be delivered, the storage capacity of the transportation 3014, the type of fuel utilized by the transportation 3014 (renewable, fossil fuel, biofuel, etc.), and/or the length of time required for crop feedstock delivery. In further embodiments, data related to crop feedstock source related data and/or transportation related data may be stored in a database, in one or more controllers including a procurement controller, a procurement computing device, a procurement and distribution controller, and/or a procurement and distribution computing device. In related aspects, biofuel integration controller 3002 may collect data and choose the options, pathway(s) and/or processes from these devices.

Figure 5:
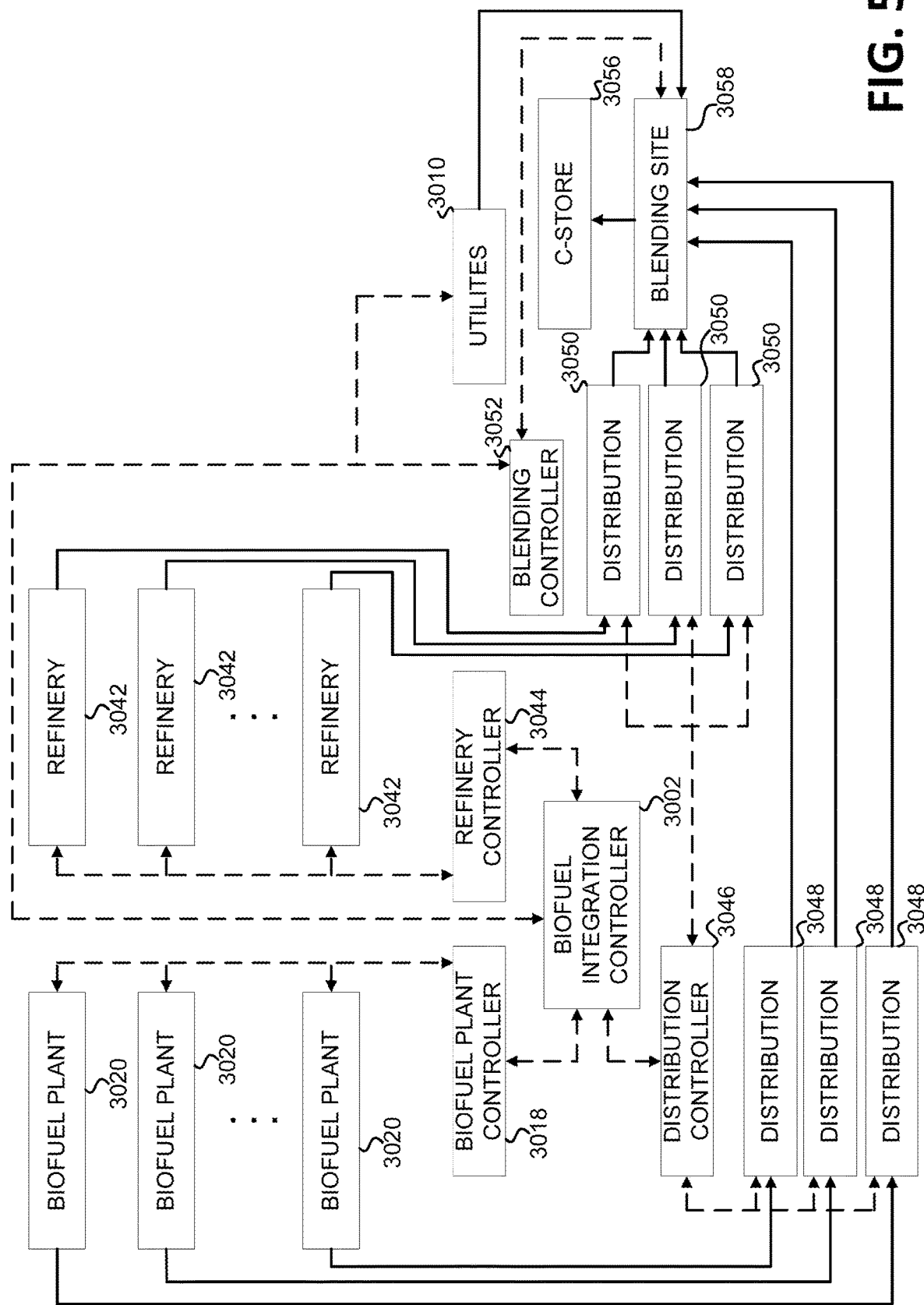
FIG. 5 is a block diagram illustrating a system for managing low carbon intensity biofuel production according to embodiments of the disclosure.

As illustrated in FIG. 5, the biofuel integration controller 3002 may control and select different biofuel production processes at a biofuel plant 3020. Biofuel plant 3020 may be operably connected to a biofuel integration controller 3002, which itself may be operably connected to one or more biofuel plants 3002 and/or refineries 3042 operably connected to refinery controller 3044 for, e.g., blending biofuels using blending controller 3052 produced in accordance with the present disclosure with traditional, fossil fuels and other carbonaceous fuels. In such examples, biofuel integration 3002 may include a CI threshold for a particular refined and biofuel-blended transportation fuel. In accordance with the CI, biofuel integration controller 3002 may select an amount of biofuel at a particular CI and an amount of traditional/transportation fuel at a particular CI. Biofuel integration controller 3002 may determine the types of biofuel distribution pathways 3048 (similar to transportation 3014) and transportation fuel distribution pathways 3050 and the CI associated with each. On the basis of these CI values, biofuel integration controller 3002 may choose an optimal distribution pathway or pathways. Following transit to the blending site 3058, biofuel integration controller 3002 or blending controller 3052 may initiate blending of refined transportation fuel and biofuel, e.g. at blending site 3058. The resulting refined and blended transportation fuel may subsequently be transported to a convenience store 3056 as a low CI blended transportation fuel.

In aspects, several of the components of the biofuel production process and/or transportation fuel process may be co-located or located at proximal locations, e.g., for beneficially reducing CI. For instance, one of the biofuel plants 3020 may be co-located with or proximate to one of the crop feedstock sources of one or more of a regenerative farm and/or a refinery 3042, and may further be co-located with or proximate to multiple regenerative farms and/or refineries 3042. Additionally, each location may further comprise one or more various storage structures/tanks for storing one or more crop feedstock(s), refined transportation fuels, biofuel, biofuel additives, byproducts, etc.

Figure 6:
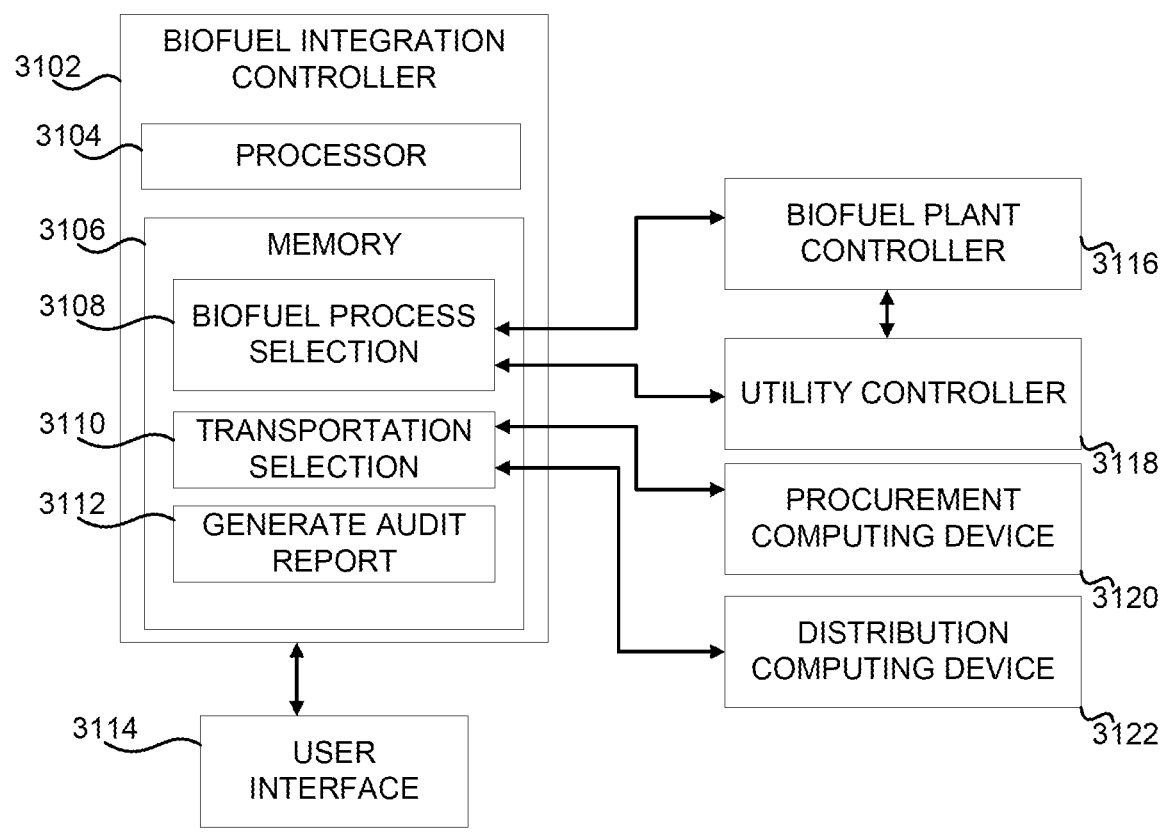
FIG. 6 is a simplified diagram illustrating a control system for managing low carbon intensity biofuel production in accordance with certain embodiments of the present disclosure.

FIG. 6 is a simplified diagram illustrating a control system for the management of a low carbon intensity (CI) biofuel production in accordance with embodiments of the present disclosure. FIG. 6 illustrates aspects of a biofuel integration controller 3102 for managing low CI biofuel production. As described above, biofuel integration controller 3102 may, in certain aspects, manage or control the operations associated with production, including low and/or high CI biofuel production processes and/or operations. The biofuel integration controller 3102 may consist of one or more controllers, including but not limited to a supervisory controller, a programmable logic controller (PLC), a computing device (e.g., a laptop, a desktop computing device, and/or a server such as a cloud server), and/or related devices. In some embodiments, biofuel integration controller 3102 may be positioned at or near a biofuel production facility. In aspects where biofuel integration controller 3102 consists of multiple controllers, biofuel integration controller 3102 may be located near or at various crop feedstock sources including one or more regenerative farms, near or at one or more biofuel production facilities, and/or at other strategic off-site locations. In additional embodiments, biofuel integration controller 3102 may include at least one processor 3104, as well as memory 3106. In some aspects, the memory 3106 may include instructions. In a non-limiting example, memory 3106 may consist of a machine-readable storage medium.

Biofuel integration controller 3102 may consist of, store, or include various modules or instructions in memory 3106 capable of performing various tasks when executed by processor 3104. The modules may, in certain embodiments, include or define a set of instructions capable of being executed by processor 3104 for different aspects involved in managing low and/or high CI biofuel production. The one or more modules may be in operable communication, e.g., in signal communication, with one or more controllers, sensors, data inputs, computing devices, servers, biofuel production facility components, additional user interfaces and combinations thereof. Biofuel integration controller 3102 may, in further aspects, consist of a biofuel process selection module 3108, a transportation selection module 3110, a crop feedstock source selection module, and an audit report module 3112, as well as combinations of the foregoing. Biofuel process selection module 3108 may, in embodiments, be in signal communication with biofuel plant controller 3116 and/or utility controller 3118, as well as in signal communication with one or more biofuel plant controllers, wherein each biofuel plant controller may be located at a unique biofuel plant. Moreover, biofuel process selection module 3108 may be in signal communication with biofuel plant controller 3116, and further include the functionality of utility controller 3118. In further embodiments, biofuel integration controller 3102 encompasses the functionality of a biofuel plant controller 3116 and/or a utility controller 3118. In certain aspects, transportation selection module 3110 may be in operable connection with one or more of procurement computing device 3120, distribution computing device 3122, a procurement and distribution computing device, a controller, a user interface, a server, database, another device, and combinations thereof. The transportation selection module 3110 may, in additional aspects, include functionality for selecting crop feedstock(s) from a crop feedstock source derivable from one or more regenerative farming operations, including a separate module operating functionally as a crop feedstock selection module. In some aspects, audit report module 3112 may be in signal communication with a user interface 3114 such that a user may directly request an audit report using user interface 3114. The user interface 3114 may further be in signal communication with biofuel integration controller 3102 and/or the audit report module 3112 where, in a non-limiting example, user interface 3114 may transmit and receive data to and from biofuel integration controller 3102.

In some embodiments, user interface 3114 may consist of one or more inputs such as a keyboard, a mouse, a touchscreen, a graphical user interface (GUI) and/or a display. In additional aspects, the user interface 3114 may be a computing device, such as a laptop, desktop computer, server, smartphone, tablet, a terminal or a combination of one or more of the foregoing. In aspects, a user is capable of entering data into user interface 3114 for conveyance to biofuel integration controller 3102. For instance, a user may enter data such as a threshold CI for a certain biofuel production process such as a low CI biofuel specification for a particular biofuel, renewable diesel, biodiesel, biogasoline, biokerosene, biofuel oil, etc., production process, where the low CI biofuel specification includes the targeted threshold CI. The low CI biofuel specification may be or may include the definition of a low CI biofuel. Alternatively, a similar process may be undertaken for instances where production of a high or higher CI biofuel may be required. In still further aspects, a user may prompt or initiate a biofuel production process such as a biofuel production process lacking a specific, threshold CI.

In embodiments, biofuel integration controller 3102 may be connected to one or more databases, including a database storing data directed to a threshold CI. Biofuel integration controller 3102 may then obtain the threshold CI from the database for a particular biofuel production process. Biofuel integration controller 3102 may include or store the threshold CI in memory 3106. In additional embodiments, a user may enter or input other data into biofuel integration controller 3102 via user interface 3114, which may include but is not limited to available crop feedstock(s), available crop feedstock(s) transportation pathway(s), available biofuel production processes at biofuel plants, available utilities, available biofuel distribution pathways and combinations thereof. A user may further enter or input algorithms and/or calculations for determining a CI directed to any process of interest.

In some aspects, in response to a reception of a threshold CI, whether from user interface 3114, a database, another device, or from memory 3106, biofuel integration controller 3102 may set, assign and/or utilize the threshold CI as a current threshold CI for a particular biofuel production process. Accordingly, biofuel integration controller 3102 may be capable of selecting various portions of the biofuel production process to ensure that the desired threshold CI is not exceeded or diminished. Biofuel integration controller 3102 may further simulate, model and/or determine many different variations to determine the best possible path, combination and/or selection based on various data points or factors, including cost, demand, shortest amount of time from crop feedstock(s) to biofuel, overall or total CI, etc. In further embodiments, and as opposed to utilizing a set CI or threshold CI, biofuel integration controller 3102 may initiate biofuel production based on the lowest possible CI on the basis of all available options including the lowest possible cost, the shortest amount of time to produce the biofuel, the present or anticipated demand for a particular biofuel (e.g., low CI), and combinations thereof. Biofuel integration controller 3102 may, in certain aspects, determine the best possible path, combination, or selection via multiple decision making processes including but not limited to a brute-force method, a min-max method, an admissible decision method, and additional methods known to the skilled artisan.

For instance, upon receipt of a threshold CI or a prompt for initiation, biofuel integration controller 3102 may determine a CI for a select number of or all available selections of one or more available crop feedstock(s). Biofuel integration controller 3102 may further determine a CI for a number of or all selections of blends of the one or more available crop feedstock(s). A crop feedstock(s) selection module, biofuel integration controller 3102, transportation selection module 3110, as well as combinations thereof and/or additional available module(s), may subsequently perform the CI determination for the crop feedstock variations associated with the CI of obtaining a particular crop feedstock or feedstocks from one or more regenerative farms. The crop feedstock(s) selection module, biofuel integration controller 3102, transportation selection module 3110 and any additional module(s) may be utilized to determine the CI of each crop feedstock variation (where such variations are incorporated) based on data received from procurement computing device 3120, a procurement and distribution computing device, a database, one or more user inputs from user interface 3114, a crop feedstock(s) source controller in signal communication with biofuel integration controller 3102, memory 3106 and/or an additional device or devices used for storing such data. The data received may, in particular aspects, include a volume of a crop feedstock(s), a type or types (where applicable) of crop feedstocks, and/or a physical location of the crop feedstock(s) (for example, city, state, country, etc.). The data may further consist of a CI (or raw data for assisting in the determination of the CI) associated with producing, obtaining, and/or any other processing of the crop feedstock(s), such as a CI associated with obtaining, procuring, and/or processing one or more crop feedstock(s) from a crop feedstock source such as a regenerative farm. Once a number of or all of the associated crop feedstock CIs are determined, biofuel integration controller 3102 may store each CI in memory 3106, at one or more databases and/or at procurement computing device 3120 for future utilization.

Biofuel integration controller 3102 may further determine a crop feedstock transportation CI for an individual, a number of, or all available crop feedstock transportation pathways for each or a number of each crop feedstock variation or variations. In aspects, transportation selection module 3110 or another module in biofuel integration controller 3102 may determine the CI. In further aspects, biofuel integration controller 3102 and/or transportation selection module 3110 may determine the crop feedstock transportation CI(s) based on the selected (one or more) available crop feedstock(s) or crop feedstock variations, for any particular iteration or determination. For instance, if a foreign or overseas crop feedstock is selected, railway and/or marine delivery modes or pathways may be considered and optimized, where locally available crop feedstock(s) and/or crop feedstocks available within the same country may consider and utilize railway and truck transportation options. Biofuel integration controller 3102 and/or transportation selection module 3110 may obtain available crop feedstock transportation pathways using procurement computing device 3120, user interface 3114, one or more databases, memory 3106, another device and combinations thereof. Additionally, biofuel integration controller 3102 and/or transportation selection module 3110 may base the CI on the volume of each crop feedstock transportation pathway, the type of fuel utilized in the crop feedstock transportation pathway or pathways (such as gas, electric, steam, additional liquid fuels including biofuels, etc.), and/or the distance associated with delivery of the crop feedstock(s) to the biofuel plant. After one, a number of or all of the crop feedstock transportation pathway variation CIs are determined, biofuel integration controller 3102 may store each CI in memory 3106, in one or more available databases, and/or at procurement computing device 3120.

In additional embodiments, biofuel integration controller 3102 may utilize biofuel process selection module 3108 to determine a biofuel production process and/or utilities CI for a number of or all available biofuel production processes at available biofuel plants and/or utility options for each or a number of each crop feedstock variations. Biofuel integration controller 3102 may, in alternative aspects, determine a biofuel production process CI and/or a utilities CI. Biofuel process selection module 3108 or other modules within biofuel integration controller 3102 may determine, in embodiments, biofuel production processes and/or utilities CI. In accordance with the foregoing, a biofuel production process may utilize any available utilities for advantageously mitigating and/or eliminating carbon emissions for standard biofuel production processes. For example, renewable utilities such as solar, wind, geothermal, renewable gas, etc. may be utilized in the biofuel production process for beneficially reducing overall CI, carbon emissions, deleterious byproducts, etc. Moreover, in non-limiting embodiments carbon sequestration may be utilized or selected to reduce or offset the CI for a particular biofuel production process or processes for advantageously reducing the overall CI for biofuel production. For example, biofuel integration controller 3102 or biofuel process selection module 3108 may be utilized to determine available biofuel production processes and utilities based on options available from biofuel plant controller 3116, utility controller 3118, memory 3106 and/or combinations thereof.

In further aspects, biofuel integration controller 3102 and/or biofuel process selection module 3108 may independently or in tandem be utilized to assess available biofuel production processes, utilities, etc., based on the selected one or more available crop feedstock(s) or crop feedstock variations, wherein biofuel integration controller 3102 and/or biofuel process selection module 3108 may be used to determine the CI for each available biofuel production process and utility option for each available crop feedstock variation. In embodiments, biofuel integration controller 3102 and/or biofuel process selection module 3108 may determine the CI for each available biofuel production process and utility option based on the type or types of the selected crop feedstock variations, the utilities to be used during the biofuel production process or processes, the yield associated with each biofuel production process, and/or additional determinants known to those of skill in the relevant art. Biofuel integration controller 3102 may, in still further aspects, consider the utilization of additional biofuel plants, including aspects where biofuel integration controller 3102 determines a CI for one or more biofuel plants as described above. Once a number of or all of the biofuel production processes and utilities CI (for one or more biofuel plants), based on the available crop feedstock variations, are determined, biofuel integration controller 3102 may store each CI in memory 3106 and/or one or more databases for future use.

In accordance with the foregoing, biofuel integration controller 3102 may, as opposed to determining a biofuel production process and utility CI, determine a biofuel production process CI and/or a utilities CI. The utility CI may be based on the utilities available for use and associated with a particular biofuel production process, the utilities used to store one or more crop feedstock(s), the utilities used to store biofuel, other utilities used for various other processes at available biofuel plants, and/or at other points in the biofuel production process and pathway.

Biofuel integration controller 3102 may, in further embodiments, determine a biofuel distribution CI for a number of or all available biofuel distribution pathways for each or a number of each crop feedstock and variations associated therewith. For instance, transportation selection module 3110 or another module in biofuel integration controller 3102 may determine the biofuel distribution CI. Biofuel integration controller 3102 or transportation selection module 3110 may determine the biofuel distribution CI based on, e.g., the selected one or more available crop feedstock(s) and biofuel production process yield(s), for any particular or associated iteration and/or determination. In non-limiting embodiments, a biofuel production process for a particular feedstock variation or variations may produce a certain volume of biofuel and associated byproducts, which may differ from a separate biofuel production facility and associated process/pathway. Biofuel integration controller 3102 or transportation selection module 3110 may further receive and assess available biofuel distribution pathways from distribution computing device 3122, user interface 3114, one or more databases, memory 3106, another device and combinations thereof. Moreover, biofuel integration controller 3102 and/or transportation selection module 3110 may determine the biofuel distribution CI based, e.g., on the volume of each biofuel distribution pathway, the fuel type utilized by each biofuel distribution pathway (renewable, fossil fuel, etc.), and/or the distance from the biofuel plant to the distribution point and/or an end destination/point such as a convenience store. The determination of a number of or all of the biofuel distribution pathway variation Cis (based on, e.g., crop feedstock variation(s) beneficially allows biofuel integration controller 3102 to store each CI in memory 3106, at one or more databases, in distribution computing device 3122, and/or procurement and distribution computing device(s) for future use and modification as necessary.

In some aspects, the determination of a number of or all CIs for each selection (e.g. selection of the one or more available crop feedstock(s), the crop feedstock(s) transportation pathway, the biofuel production process and utilities, the biofuel distribution, and/or blending processes) may allow ethanol integration controller 3102 to determine a set of variations, combinations, or selections of each of the selections exemplified herein. For instance, one set of the variations, combinations and/or selections may include one or more available crop feedstock(s), one or more available crop feedstock transportation pathways (which may correspond to the available crop feedstock variation(s)), one or more biofuel production processes (corresponding to the crop feedstock variation(s)), one or more utilities (corresponding to the biofuel production processes and/or other utility based processes), and/or one or more biofuel distribution pathways (corresponding to the biofuel produced by the biofuel plant). Biofuel integration controller 3102 may further determine a total CI for each variation, combination, or set of selections. In non-limiting embodiments, biofuel integration controller 3102 may determine the total CI based on, e.g., the volume of the selected one or more available crop feedstock(s), the yield from the corresponding or selected biofuel production processes to produce biofuel, the determined crop feedstock(s) CI(s), the determined crop feedstock(s) transportation CI(s), the determined biofuel production process and utilities CI, the determined biofuel distribution CI and combinations thereof. In additional aspects, factors such as the total CI of crop feedstock storage CI (if utilized), a biofuel tank CI (if utilized), emissions (e.g., volatile organic chemical (VOC) emissions through working losses, breathing losses, flashing losses and related emissions), any utilized carbon sequestration, the CI of one or more byproducts associated with the biofuel production process (which may or may not decrease the overall CI), other carbon offsetting practices known to the skilled artisan and combinations thereof may be considered when determining a total CI as will be understood by those skilled in the art may be considered when determining a total CI. Accordingly, once biofuel integration controller 3102 determines the total CI for each variation, it may store each total CI in memory 3106 and/or at one or more databases.

Following the determination of each total CI variation, biofuel integration controller 3102 may determine a selection from the available set of combinations. In embodiments, the available combinations may include the various selections described herein, with a CI that is less than the threshold CI. If there are no variations with a CI less than the CI threshold, biofuel integration controller 3102 may notify a user that all selections exceed the threshold CI, prompt a user to enter a new threshold CI, and/or prompt a user to accept the selection with the lowest total CI (which may exceed the threshold CI). Alternatively, biofuel integration controller 3102 may automatically select a new threshold CI. In another embodiment, biofuel integration controller 3102 may determine the selection based on the lowest total CI not exceeding the threshold CI. In further embodiments, multiple combinations may include a similar or the same (total) CI. However, each combination may be characterized by differing properties, including but not limited to a financial issue and/or a temporal issue such as from crop feedstock(s) to customer. In such embodiments, biofuel integration controller 3102 may select one of the combinations, with a similar or a CI lower than the threshold, on the basis of the time of availability of each of the selected one or more available crop feedstock(s), a time for delivery to the biofuel plant (or plants) by the crop feedstock transportation pathway(s), a processing time or times associated with crop feedstock(s) utilizing the selected one or more biofuel production processes, a time to delivery from the biofuel plant to the end user (such as a blending site, etc.), and/or any biofuel production processes that may be queued or in the process of production. Upon determination of a selection, biofuel integration controller 3102 may initiate biofuel production or transmit a request to confirm initiation of biofuel production.

Biofuel integration controller 3102 may, in embodiments, determine a combination of a selection of one or more crop feedstock(s), one or more crop feedstock transportation pathways, one or more biofuel production processes, one or more utilities, and/or one or more biofuel distribution pathways. In some aspects, biofuel integration controller 3102 may determine a combination based on crop feedstock CI (based on, for example, a ratio or blend of available crop feedstock volume and type), crop feedstock transportation CI (based on, e.g., available crop feedstock transportation delivery distance and fuel type), biofuel production process CI (based on, for instance, the type of biofuel production process, the volume and type of crop feedstock, the length of time of the biofuel production process, and/or the yield of the biofuel production process), the utility CI of one or more utilities (based on the type of utility utilized in the biofuel production process and the distance the utility travels to reach the biofuel plant), and/or biofuel distribution CI (based on available biofuel distribution delivery distance and fuel type). Additional determinants and factors may be utilized in determining a combination, including but not limited to the cost of each process, the margin or profit based on a sale of the final biofuel product, availability, yield, and/or one-time costs (such as increasing biofuel production capacity and/or increasing efficiency of an aspect of the biofuel production facility or source, etc.).

In further embodiments, biofuel integration controller 3102 may be in operable connection to one or more databases, which may comprise various data points including available crop feedstock(s) (and corresponding raw data), available transportation modes (and corresponding raw data), available and types of storage tanks (and corresponding raw data), available biofuel production processes (and corresponding raw data), and/or available utility options (and corresponding raw data). In related aspects, a user may update, via user interface 3114, the data stored at the database or databases, and may further update the data at the database(s), for example, based on data received from various controllers and/or computing devices. In another embodiment, biofuel integration controller 3102 may store determined CIs, total CIs, and/or audit reports at the one or more databases, which may be optionally and selectively made available to additional devices or user interfaces.

Figure 7:
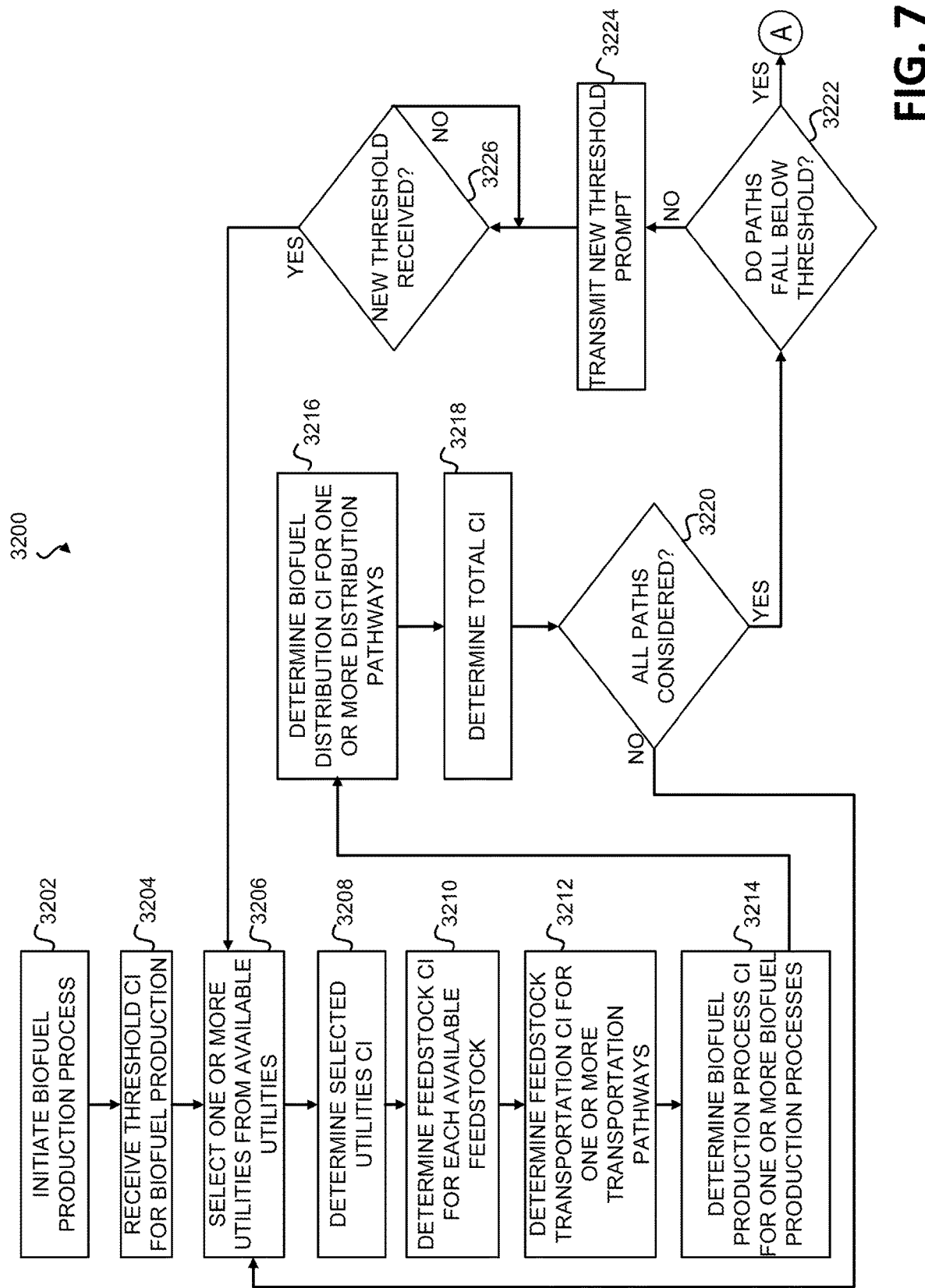
FIG. 7 is a flow diagram, implemented in a controller, for managing low carbon intensity biofuel production according to embodiments of the disclosure.
Figure 8:
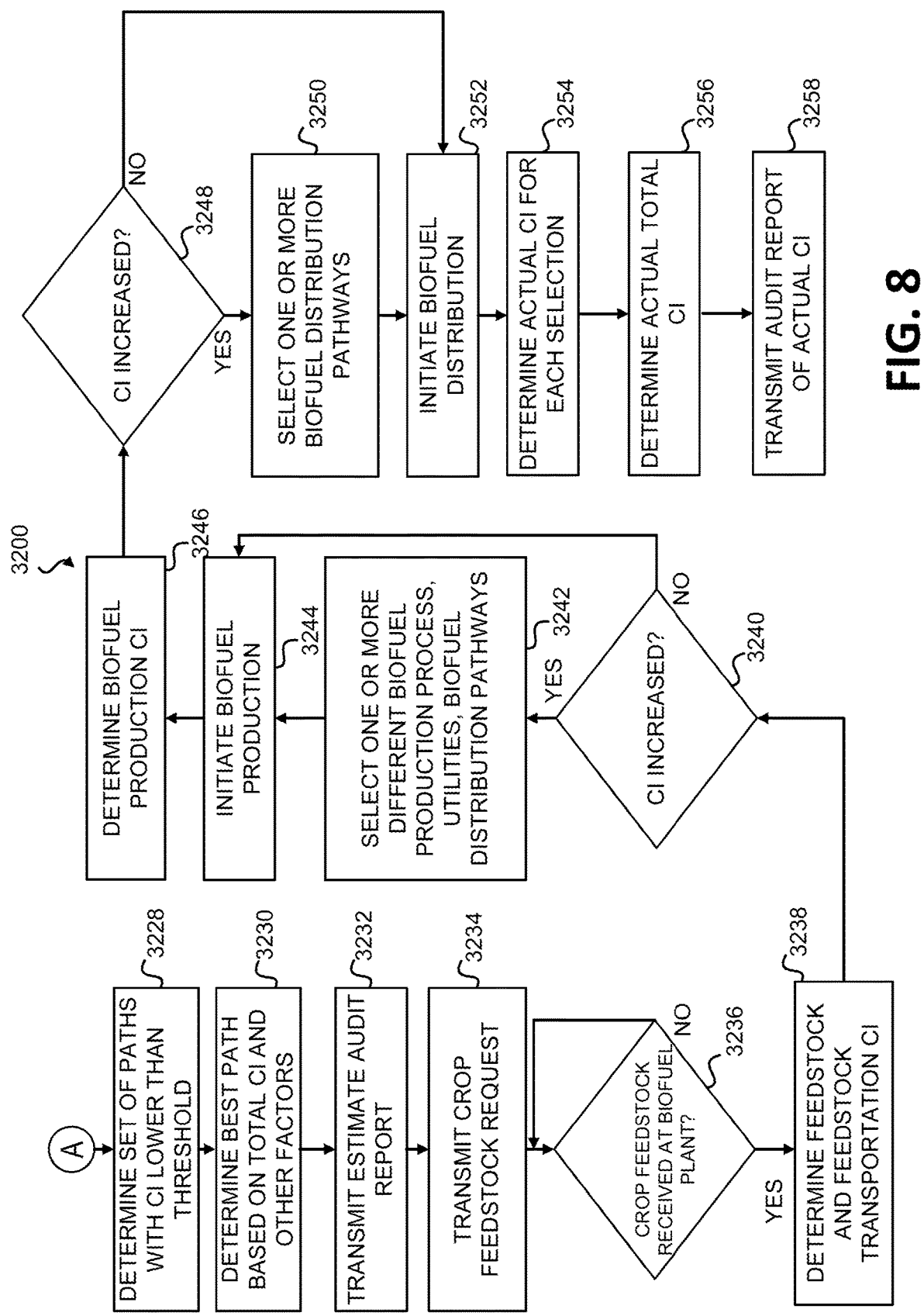
FIG. 8 is a flow diagram, implemented in a controller, for managing low carbon intensity biofuel production in accordance with certain embodiments of the present disclosure.
Figure 9:
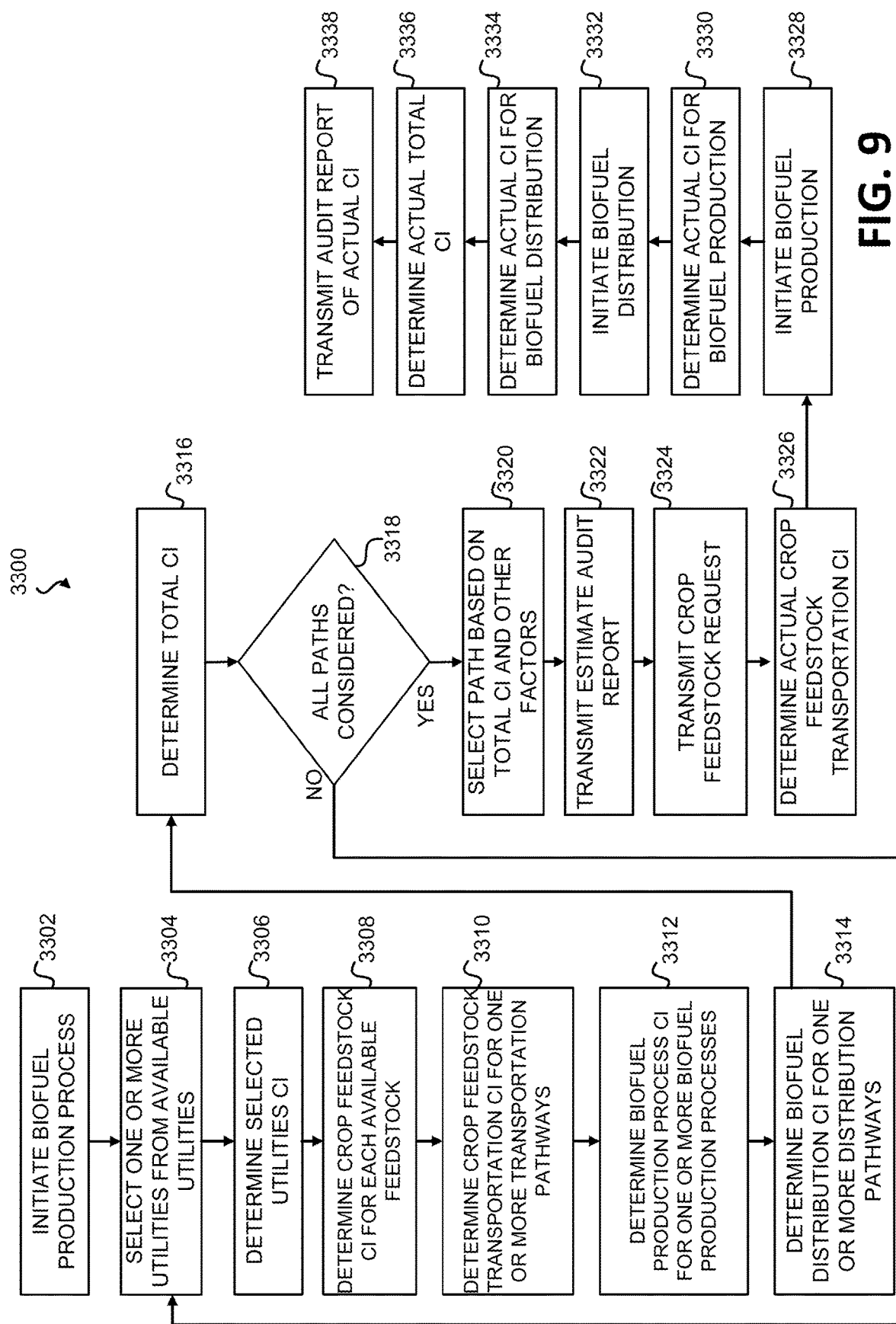
FIG. 9 is a flow diagram, implemented in a controller, for managing low carbon intensity biofuel production according to embodiments of the disclosure.

FIGS. 7-9 are flow diagrams, implemented in a controller, for managing the low carbon intensity ethanol production, according to an embodiment. The methods detailed in the flow diagrams are made in reference to biofuel integration controller 2902 and system 2900 as disclosed in FIG. 3. Unless otherwise specified, the actions of method 3200 (FIGS. 7-8) and method 3300 (FIG. 9) may be completed using biofuel integration controller 2902. Additionally, method 3200 and method 3300 may be included in one or more programs, protocols and/or instructions loaded into the memory of biofuel integration controller 2902 or in one or more additional controller(s) and executed on the processor or one or more processors of the biofuel integration controller 2902 or additional controller(s). The non-limiting order in which the operations are described may be combined in any order and/or in parallel to implement the disclosed methods using any disclosed component et al.

In accordance with block 3202, biofuel integration controller 2902 may receive a signal or prompt for initiating a biofuel production process. Alternatively, a user at a user interface such as a GUI may initiate the biofuel production process. At block 3204, biofuel integration controller 2902 may receive a threshold CI for an amount of biofuel to be produced during a biofuel production process. Biofuel integration controller 2902 may then receive the threshold CI from a user, a user interface (e.g. a GUI), a low CI biofuel specification (including but not limited to an input by a user or stored in a database), a controller or controllers, memory of biofuel integration controller 2902, an additional biofuel integration controller, a supervisory controller, and/or another operably-connected device. In response to receipt of the threshold CI, biofuel integration controller 2902 may utilize or assign the input threshold CI as a current threshold CI, which may correspond to a particular biofuel production process or operation such that a threshold CI may vary for various biofuel production processes.

At block 3206, biofuel integration controller 2902 may select one or more utilities 2912 for operating biofuel plant 2908 and/or biofuel plants from available utilities. In embodiments, biofuel integration controller 2902 may determine utilities 2912 that are available based on, e.g., data available from a utility controller at a utility provider, data stored in the biofuel integration controller 2902, one or more databases and/or from the memory of a biofuel plant controller and/or additional controllers. In a non-limiting example, a dedicated power source (a renewable power source such as a wind farm, a traditional power source fueled by fossil fuel, or a combination of such power sources) may be located at or near biofuel plant 2908. In further aspects, biofuel plant 2908 may comprise a variety of power sources or access to power sources, and accordingly, utilities 2912 may be the largest factor or among the largest factors contributing to the overall CI of the biofuel production process. In response, biofuel integration controller 2902 may therefore select a lower CI utility or combination of utilities, including the lowest available CI utility or utilities. Accordingly, at block 3208 biofuel integration controller 2902 may determine the selected utilities CI or may then select different one or more utilities 2912 and determine the various CI for selections of the biofuel production processes (e.g., determining CI for each variation, combination, or path). In accordance with certain aspects, biofuel plant 2908 operations may be offset by the use of low CI utilities. For instance, renewable fuels from a utility provider may be provided to biofuel plant 2908 to process a crop feedstock or feedstocks. Utilities 2912 may include different sources or forms of water/steam, electricity (including solar, wind, geothermal, renewable gas, etc.), and/or of other fuels such as natural gas, and additional utilities such as hydroelectric utilities and hydrogen fuel cell based systems. For instance, a utility provider may consist of an energy producing facility connected to the grid, an energy producing facility nearby or proximate to biofuel plant 2908 or an energy production facility nearby or at and dedicated to biofuel plant 2908, and may produce energy using renewable resources, such as a wind or a solar farm located nearby or at biofuel plant 2908. In additional aspects, the utility provider may produce energy via fossil fuels, renewable resources or a combination thereof. The utilities CI may further include a CI associated with utilities 2912 used throughout biofuel plant 2908. The utilities CI may be further based on utilities 2912 used at the crop feedstock source, i.e. the regenerative farm, used at the fermentable feedstock storage tank 2906 and/or used at any other point in the biofuel production process. In another embodiment, the biofuel integration controller 2902 may determine the CI as a function of the carbon emissions per unit energy associated with the available utilities, the procurement of the available utilities, and/or the generation of the available utilities.

Turning to block 3210, in embodiments biofuel integration controller 2902 may determine the CI for one or more available crop feedstocks from a crop feedstock source 2904. As previously noted above, the available crop feedstock(s) may include organic matter including feedstocks beneficially comprising starches and/or sugars, including but not limited to soybean, corn, barley, wheat, sugarcane, beets, et al., as well as additional crop feedstocks such as rapeseed, canola, mustard, sunflower, safflower, castor bean, jatropha and oilseed crops such as lesquerella and pennycress, from a variety of sources. In some aspects, biofuel integration controller 2902 may determine a list or set of available feedstock(s) that may be provided by a user input via one or more of a user interface (e.g., a GUI), a database, a procurement controller, a procurement computing device, a procurement and distribution computing device, memory associated with biofuel integration controller 2902 and/or another device. Further, data or information on available crop feedstock(s) may comprise a subset of data or information on all available crop feedstock(s) based on available biofuel plants that may optionally be set up to accommodate processing for one or more particular crop feedstock(s). Accordingly, biofuel integration controller 2902 may determine crop feedstock CI for one or more available crop feedstock(s) from the subset of available crop feedstock(s). In further aspects, the type and/or location of the crop feedstock(s) (e.g., the distance of a crop feedstock from biofuel plant 2908, etc.), the power used or emissions generated by obtaining or producing the crop feedstock and/or foodstuffs produced therefrom and/or the CI of fertilizer used for the crop feedstock(s). In a further example, the CI may be determined as a function of the carbon emissions per unit energy for each of the factors associated with a selected crop feedstock(s). In still further aspects, the crop feedstock(s) CI may be determined based on the ratio of the determined or selected one or more available crop feedstocks, such as the ratio of the CI of the two or more different crop feedstocks. In yet another embodiment, the CI associated with procuring the selected feedstock at the source may include a carbon intensity of the selected feedstock and a carbon intensity for providing the feedstock at the source. In other embodiments, the function of carbon emissions per unit energy associated with procuring the selected feedstock at the source may include carbon emissions per unit energy of the selected feedstock, as well as carbon emissions per unit energy for providing the feedstock at the source.

At block 3212, in embodiments biofuel integration controller 2902 may determine a crop feedstock transportation CI for each available crop feedstock transportation pathway for the one or more available crop feedstock(s). The available crop feedstock transportation pathways may include marine vessel transportation, vehicular transportation (including but not limited to a commercial truck), and/or rail transportation. In accordance with embodiments of the instant disclosure, crop feedstock(s) may be delivered via one or more particular crop feedstock transportation pathways. Accordingly, and based on one or more available crop feedstock(s), biofuel integration controller 2902 may determine the crop feedstock transportation CI(s). Biofuel integration controller 2902 may further determine the crop feedstock transportation CI for each available crop feedstock transportation pathway or pathways based on the volume of the crop feedstock transportation pathway, the fuel utilized by the crop feedstock transportation pathway, and the distance the crop feedstock transportation pathway is required to travel to deliver the crop feedstock to biofuel plant 2908. In an example, the CI may be determined as a function of the carbon emissions per unit energy for each selected feedstock transportation pathway.

In accordance with block 3214, biofuel integration controller 2902 may determine the biofuel production process CI and/or the CI for other biofuel plants. In such instances, biofuel integration controller 2902 may obtain a list of available biofuel plant processes from a biofuel plant controller at, for example, biofuel plant 2908 or additional biofuel plants, one or more database, the memory of biofuel integration controller 2902 or additional sources as disclosed herein. Moreover, biofuel integration controller 2902 may determine the biofuel production processes CI for each biofuel production process based on the type of crop feedstock(s) selected and the yield of the biofuel production process (e.g., in a non-limiting example, as a function of the carbon emissions per unit energy for each biofuel production process). In accordance with the foregoing, high CI biofuel plant operations or processes may be offset by the use of beneficial offsetting practices including but not limited to carbon sequestration, as will be understood by the skilled artisan.

Turning to block 3216, biofuel integration controller 2902 may determine a biofuel distribution CI for each available biofuel distribution pathway for biofuel from a biofuel plant 2908. The available biofuel distribution pathways may include one or more of marine vessel transportation, commercial truck or vehicular transportation, and/or rail transportation. Biofuel integration controller 2902 may further determine the biofuel distribution CI for each available biofuel distribution pathway based on the volume of the biofuel distribution pathway, the fuel utilized by the biofuel distribution pathway, and the travel distance associated with the biofuel distribution pathway may travel to deliver the biofuel from biofuel plant 2902 to optional blending site 2914 or another end user location. In a non-limiting example, the biofuel distribution CI may be determined as a function of the carbon emissions per unit energy for each biofuel production process.

In accordance with block 3218, biofuel integration controller 2902 may determine the total CI for each variation of selections noted above. For example, for the selected one or more available utilities and/or crop feedstock(s), biofuel integration controller 2902 may determine total CI based on a first crop feedstock selection, a crop feedstock transportation pathway, a first biofuel production process, a first utility, and/or a first biofuel distribution pathway. Biofuel integration controller 2902 may then determine the total CI for the next variation, etc. Biofuel integration controller 2902 may further base the total CI on the volume of the selected one or more available crop feedstock(s), the yield percentage of the biofuel plant (i.e., the volume of biofuel produced per the original feedstock volume), and/or the CI of each selection. Additional factors may optionally be taken into account for determining total CI.

In response to a determination of total CI, at block 3220, biofuel integration controller 2902 may determine whether one selection, a number of selections or all selections of the one or more available utilities (and the variations of the other selections described above) have been sufficiently considered for determining if a total CI has been determined for all variations of utility combinations or paths. If all selections or a number of selections of the one or more available utilities and/or crop feedstock(s) have not been sufficiently considered, at block 3220, biofuel integration controller 2902 may select another of the one or more available utilities or crop feedstock(s) and determine total CI as described herein. If all of the one or more available utilities and/or crop feedstock(s) or, at least, a particular amount or set of the one or more available utilities or crop feedstock(s) have been considered, biofuel integration controller 2902, at block 3222, may subsequently determine whether any path, combination, variation and/or final selection does not exceed the threshold CI. If no path, combination, variation and/or final selection does not exceed the threshold CI, biofuel integration controller 2902 may prompt a user to select a new threshold CI. In additional aspects, biofuel integration controller 2902 may automatically increase the threshold CI based on a specified amount. Biofuel integration controller 2902, at block 3226, may further wait until a new threshold CI is received by biofuel integration controller 2902, at which time the current threshold CI is set to the new threshold CI and, in accordance with block 3206, another of the one or more available utilities or crop feedstock(s) may be selected and each iteration or a number of iterations may be determined again in accordance with the foregoing.

If it is determined that at least one path, combination, variation, or final selection does not exceed the threshold CI, at block 3228, biofuel integration controller 2902 may determine a set of paths, combinations, variations, or selections with the lowest total CI. In embodiments, one path, combination, variation and/or selection may not exceed the threshold CI, while in other cases many paths or selections may not exceed the threshold CI. Each path, combination, variation and/or selection may include a selected one or more available crop feedstock(s), one or more selected crop feedstock transportation pathways, one or more selected biofuel production operations or processes, one or more selected utilities and/or one or more selected biofuel distribution pathways, as well as a corresponding CI for each selection.

Based on the set of paths, combinations, variations, or selections, at block 3230, biofuel integration controller 2902 may determine a selection of a path, combination, variation, or selection from the set of paths or selections. Biofuel integration controller 2902 may select the path, combination, variation, or selections based on, in addition to lowest total CI, time of availability of each of the selected one or more available crop feedstock(s), delivery time to the one or more biofuel plants by the crop feedstock transportation pathway, process time for a crop feedstock utilizing the selected one or more biofuel production operations or processes, delivery time from the one or more biofuel plants to an end user, etc. In a non-limiting example, biofuel integration controller 2902 may select the path, combination, variation, or selection having a lower than threshold CI (although not necessarily the lowest CI) and more efficient pathway (e.g., from crop feedstock to customer), as described above. An efficient pathway may comprise factors such as a shorter distance to travel overall (e.g., from crop feedstock source to an end user), the time of availability for the crop feedstock, the length of time to process a particular crop feedstock and derivative byproducts including foodstuffs derived therefrom, cost issues associated with each of the selections, and/or a high demand for a biofuel or blended biofuel of a particular CI.

In response to determination of a selection of the path, combination, variation, or selections, at block 3232, biofuel integration controller 2902 may generate and transmit an estimated or initial audit report to a user, user interface, database, and/or other device. The audit report may comprise the CI of each selection and the total CI. The estimated audit report may include other information regarding each part of the planned or selected biofuel production process, such as where the selected crop feedstock is from, the type and volume of the selected crop feedstock, the type of crop feedstock transportation pathways (as well as other details on the crop feedstock transportation pathway), the selected biofuel production process, the estimated yield of the biofuel production process, the selected utilities, the source of the selected utilities, the type of biofuel distribution pathways (as well as other details regarding the biofuel distribution pathway), length of time for storage at any point in the process, and/or an overall timeline of the biofuel production process. In embodiments, biofuel integration controller 2902 may generate the estimated or initial audit report based on a request from a user and/or user interface.

In some aspects, biofuel integration controller 2902, at block 3238, may transmit a crop feedstock request that may include the selected one or more available crop feedstock(s) and the selected crop feedstock transportation pathway(s). Additionally, biofuel integration controller 2902 may transmit a confirmation of the crop feedstock request prior to transmitting the crop feedstock request. In certain aspects, biofuel integration controller 2902 may transmit a request for confirmation of a crop feedstock(s) request of the selected one or more available crop feedstock(s) to a user interface or a procurement computing device. In response to receiving the confirmation from the user interface, procurement computing device, etc., biofuel integration controller 2902 may transmit the crop feedstock request to a procurement computing device, procurement controller, user interface (which may include a procurement sub-routine or instructions), a procurement and distribution computing device, or other device.

At block 3236, biofuel integration controller 2902 may determine whether the crop feedstock(s) has been received at biofuel plant 2908. Once the crop feedstock(s) has been delivered to biofuel plant 2908, at block 3238, biofuel integration controller 2902 may determine the actual CI for the selected one or more available crop feedstock(s) and corresponding crop feedstock transportation pathway(s). Biofuel integration controller 2902 may determine, at block 3240, whether, in relation to the determined crop feedstock CI and crop feedstock transportation CI, the actual CI for either the selected one or more available crop feedstock(s) and corresponding crop feedstock transportation pathway(s) has increased. If an increase is determined, biofuel integration controller 2902, at block 3242, may select one or more different biofuel production processes, utilities, and/or biofuel distribution pathways to maintain the total CI, cost, and/or timeline of biofuel production, if such a selection is available. In another example, biofuel integration controller 2902 may send a prompt or notification to a user or user interface. Further, the prompt may include the available options or paths, such as one or more different biofuel production processes at one or more biofuel plants, utilities and/or biofuel distribution pathways. In such examples, the user may select the new options or paths to maintain the total CI on the basis, for instance, of the estimated audit report, or lower the total CI further. Alternatively, the user may forego the new options or paths and choose to continue with the prior selections.

In response to the determination that the determined crop feedstock CI and crop feedstock transportation CI have not increased or in response to a selection of one or more different biofuel production processes at one or more biofuel plants, biofuel integration controller 2902 may, at block 3244, initiate any selected biofuel production processes or operations. In another example, biofuel integration controller 2902 may connect to a biofuel plant controller and transmit the initiation to the biofuel plant controller. Biofuel integration controller 2902 may notify a user of the initiation of the biofuel production processes or operations. In another example, biofuel integration controller 2902 may prompt a user to initiate or confirm initiation of the biofuel production processes or operations.

In response to a reception of or determination of completion of biofuel production processes or operations, at block 3246, biofuel integration controller 2902 may determine the actual CI for the selected biofuel production processes, operations and/or utilities. Biofuel integration controller 2902 may, at block 3248, then determine whether, in relation to the determined biofuel production processes or operational CI and/or utility CI, the actual CI for the biofuel production processes, operations and utilities, including whether CI has increased. If an increase is determined, biofuel integration controller 2902, at block 3250, may select one or more different biofuel distribution pathways to maintain CI, cost, and/or timeline of biofuel production, depending on the potential availability of such options.

The selection of a new biofuel distribution pathway, or alternatively due to the lack of any such new selection, biofuel integration controller 2902, at block 3252, may transmit a distribution request or initiate distribution of the biofuel using the selected biofuel distribution pathway. The distribution request may include, e.g. the amount or volume of biofuel as well as the selected biofuel distribution pathway. In related aspects, biofuel integration controller 2902 may transmit a request for confirmation of a biofuel distribution request to a user interface and/or a distribution computing device, and biofuel integration controller 2902 may subsequently transmit the biofuel request to a distribution computing device, distribution controller, user interface procurement and/or distribution computing device, or related device(s) capable of completing the request.

At block 3254, biofuel integration controller 2902 may, in embodiments, assess the actual CI for the selected crop feedstock(s), the completed crop feedstock(s) transportation pathway(s), the completed biofuel production processes, as well as operations including but not limited to utilities and the completed biofuel distribution pathway. At block 3256, in certain aspects biofuel integration controller 2902 may determine the actual total CI, which may be based on the actual biofuel "total yield" in relation to the proportion of byproducts produced in the biofuel production process, the actual feedstock volume, the actual CI for the selected one or more available crop feedstock(s), the completed crop feedstock(s) transportation pathway(s), the completed biofuel production processes and/or operations including, e.g., utilities, and the completed biofuel distribution pathway including, e.g. delivery to consumers and commercial users.

At block 3258, biofuel integration controller 2902 may generate and transmit an actual or final audit report to a user, a user interface (i.e., a GUI), a database or another device. The audit report (actual and/or final) may include the actual total CI and the actual CI for each stage and/or for each process, such as the actual CI for the selected one or more available crop feedstocks, the completed crop feedstocks transportation pathway, the completed biofuel production processes or operations including utilities, and the completed biofuel distribution pathway(s). Biofuel integration controller 2902 may, in particular aspects, generate the actual or final audit report following receipt of one or more requests from a user and/or user interface such as a GUI.

As illustrated in FIG. 9 and at block 3302, biofuel integration controller 2902 may receive a signal or prompt to initiate a biofuel production process in accordance with the relevant aspects of FIG. 3. At block 3304, biofuel integration controller 2902 may select one or more utilities 2912 to operate biofuel plant 2908 as described herein. In accordance with block 3306, biofuel integration controller 2902 determines the CI for the selected utilities 2912. In certain aspects, biofuel integration controller 2902 may collect additional information associated with the utilities for determining a CI directed to one or more of the type of utilities, the amount of utilities to be utilized, the proximity of the utility provider to biofuel plant 2908, etc.

At block 3308, the ethanol integration controller 2902 may determine the CI for one or more available fermentable feedstock from a fermentable feedstock source 2904, as described above. At block 3310, the ethanol integration controller 2902 may determine a fermentable feedstock transportation CI for each available fermentable feedstock transportation pathway for the one or more available fermentable feedstock, as described above. At block 3312, the ethanol integration controller 2902 may determine the ethanol production process CI and/or the CI for other ethanol plants, as described above. At block 3314, biofuel integration controller 2902 may determine a biofuel distribution CI for each available biofuel distribution pathway for biofuel from biofuel plant 2908 in accordance with the relevant embodiments of FIG. 3.

At block 3316, biofuel integration controller 2902 may determine the total CI for each variation of selections as described above. As an optional step, in response to a determination of total CI, at block 3318, biofuel integration controller 2902 may determine whether all selections, a number of selections and/or one selection of the one or more available utilities (and the variations of the other selections described above) have been or should be considered (e.g., if a total CI has been determined for all variations of utility combinations or paths), as described above. In further aspects, biofuel integration controller 2902 may determine a set amount of variations or paths for a biofuel production process as opposed to determining if each variation, path and/or selection has been sufficiently considered.

In a non-limiting example, various paths may be considered, while in additional examples all paths may be considered such that, e.g., the biofuel integration controller 2902 is used to determine the CI and other data points for each variation, path, set of selections, etc., while in further examples, biofuel integration controller 2902 may strategically determine the CI and other data points for a subset of each of the available variations, paths and/or set(s) of selections. For instance, the biofuel integration controller 2902 may consider variations, paths, or sets of selections associated with one or more costs that utilize a particular crop feedstock source or sources from regenerative farm 2904, that are powered by a particular type of utility or utilities, that will be completed in a particular time frame/time period, based on the availability of a particular utility or utilities, and/or based on the availability of one or more particular crop feedstock(s). In some aspects, biofuel integration controller 2902 may, at block 3320, select the best path based on various factors, regardless of the number of paths that are considered. For instance, biofuel integration controller 2902, when determining the best available path, may consider the total CI, the cost, the timeline and/or period of time for each variation, path, or set of selections determined.

In response to determination of a selection of the path, combination, variation and/or selections, at block 3322, the biofuel integration controller 2902 may generate and transmit an estimated or initial audit report to a user, user interface (e.g., a graphical user interface (GUI)), database, and/or other device, as described herein. Moreover, in additional aspects biofuel integration controller 2902, at block 3324, may transmit a crop feedstock request, as described above. At block 3326, biofuel integration controller 2902 may determine the actual CI for the selected one or more available crop feedstock(s) and corresponding crop feedstock(s) transportation pathway, as described above. After the determination of the actual CI for the selected one or more available crop feedstock(s) and corresponding crop feedstock(s) transportation pathway, the biofuel integration controller 2902 may, at block 3328, proceed with the initiation of any selected biofuel production processes and/or operations, as described in the foregoing.

In response to a reception of or determination of completion of the selected biofuel production processes and/or operations, at block 3330, biofuel integration controller 2902 may determine the actual CI for the selected biofuel production processes, operations and/or utilities, as described in the foregoing. For example, once the actual CI for the selected biofuel production processes is determined, the biofuel integration controller 2902, at block 3332, may transmit a distribution request and/or initiate the distribution of the biofuel via the selected biofuel distribution pathway, as described herein.

In accordance with block 3334, biofuel integration controller 2902 may determine the actual CI for the selected one or more available crop feedstock(s), the completed crop feedstock transportation pathway, the completed biofuel production process or processes, or operations which include any utilities, and the completed biofuel distribution pathway, as described above. At block 3336, the biofuel integration controller 2902 may determine the actual total CI, as described above. At block 3338, biofuel integration controller 2902 may generate and transmit an actual or final audit report to a user, user interface, database, and/or other device, as described above.

This application claims priority to, and the benefit of, U.S. Provisional Application No. 63/265,686, filed Dec. 17, 2021, titled "SYSTEMS AND METHODS FOR HOLISTIC LOW CARBON INTENSITY FUEL PRODUCTION," and U.S. Provisional Application No. 63/267,636, filed Feb. 7, 2022, titled "SYSTEMS AND METHODS FOR HOLISTIC LOW CARBON INTENSITY FUEL PRODUCTION," the disclosures of which are incorporated herein by reference in their entireties.

This application is a continuation-in-part of U.S. Non-Provisional application Ser. No. 17/456,246, filed Nov. 23, 2021, titled "SYSTEMS AND METHODS OF ALTERNATIVE ENERGY INTEGRATION WITH HYDROCARBON PRODUCTS," which claims priority to, and the benefit of, U.S. Provisional Application No. 63/199,001, filed Nov. 30, 2020, titled "SYSTEMS AND METHODS OF ALTERNATIVE ENERGY INTEGRATION WITH HYDROCARBON PRODUCTS," the disclosures of which are incorporated herein by reference in their entireties. U.S. Non-Provisional application Ser. No. 17/456,246 is also a continuation-in-part of U.S. Non-Provisional application Ser. No. 17/392,600, filed Aug. 3, 2021, titled "SYSTEMS AND METHODS FOR HOLISTIC LOW CARBON INTENSITY FUEL PRODUCTION," which claims priority to U.S. Provisional Application No. 63/061,162, filed Aug. 4, 2020, titled "SYSTEMS AND METHODS FOR HOLISTIC LOW CARBON INTENSITY FUEL PRODUCTION," U.S. Provisional Application No. 63/066,912, filed Aug. 18, 2020, titled "SYSTEMS AND METHODS FOR HOLISTIC LOW CARBON INTENSITY FUEL PRODUCTION," U.S. Provisional Application No. 63/198,626, filed Oct. 30, 2020, titled "SYSTEMS AND METHODS FOR HOLISTIC LOW CARBON INTENSITY FUEL AND HYDROGEN PRODUCTION," and U.S. Provisional Application No. 63/113,186, filed Nov. 12, 2020, titled "SYSTEMS AND METHODS FOR HOLISTIC LOW CARBON INTENSITY FUEL AND HYDROGEN PRODUCTION," the disclosures of which are incorporated herein by reference in its entirety. U.S. Non-Provisional application Ser. No. 17/456,246 is also a continuation-in-part of U.S. Non-Provisional application Ser. No. 17/392,567, filed Aug. 3, 2021, titled "SYSTEMS AND METHODS FOR HOLISTIC LOW CARBON INTENSITY FUEL PRODUCTION," which claims priority to U.S. Provisional Application No. 63/061,162, filed Aug. 4, 2020, titled "SYSTEMS AND METHODS FOR HOLISTIC LOW CARBON INTENSITY FUEL PRODUCTION," U.S. Provisional Application No. 63/066,912, filed Aug. 18, 2020, titled "SYSTEMS AND METHODS FOR HOLISTIC LOW CARBON INTENSITY FUEL PRODUCTION," U.S. Provisional Application No. 63/198,626, filed Oct. 30, 2020, titled "SYSTEMS AND METHODS FOR HOLISTIC LOW CARBON INTENSITY FUEL AND HYDROGEN PRODUCTION," and U.S. Provisional Application No. 63/113,186, filed Nov. 12, 2020, titled "SYSTEMS AND METHODS FOR HOLISTIC LOW CARBON INTENSITY FUEL AND HYDROGEN PRODUCTION," the disclosures of which are incorporated herein by reference in its entirety. U.S. Non-Provisional application Ser. No. 17/456,246 is also a continuation-in-part of U.S. Non-Provisional application Ser. No. 17/392,622, filed Aug. 3, 2021, titled "SYSTEMS AND METHODS FOR HOLISTIC LOW CARBON INTENSITY FUEL AND ETHANOL PRODUCTION," which claims priority to U.S. Provisional Application No. 63/061,162, filed Aug. 4, 2020, titled "SYSTEMS AND METHODS FOR HOLISTIC LOW CARBON INTENSITY FUEL PRODUCTION," U.S. Provisional Application No. 63/066,912, filed Aug. 18, 2020, titled "SYSTEMS AND METHODS FOR HOLISTIC LOW CARBON INTENSITY FUEL PRODUCTION," U.S. Provisional Application No. 63/198,626, filed Oct. 30, 2020, titled "SYSTEMS AND METHODS FOR HOLISTIC LOW CARBON INTENSITY FUEL AND HYDROGEN PRODUCTION," and U.S. Provisional Application No. 63/113,186, filed Nov. 12, 2020, titled "SYSTEMS AND METHODS FOR HOLISTIC LOW CARBON INTENSITY FUEL AND HYDROGEN PRODUCTION," the disclosures of which are incorporated herein by reference in its entirety. U.S. Non-Provisional application Ser. No. 17/456,246 is also a continuation-in-part of U.S. Non-Provisional application Ser. No. 17/392,588, filed Aug. 3, 2021, titled "SYSTEMS AND METHODS FOR HOLISTIC LOW CARBON INTENSITY FUEL PRODUCTION," which claims priority to U.S. Provisional Application No. 63/061,162, filed, Aug. 4, 2020, titled "SYSTEMS AND METHODS FOR HOLISTIC LOW CARBON INTENSITY FUEL PRODUCTION," U.S. Provisional Application No. 63/066,912, filed Aug. 18, 2020, titled "SYSTEMS AND METHODS FOR HOLISTIC LOW CARBON INTENSITY FUEL PRODUCTION," U.S. Provisional Application No. 63/198,626, filed Oct. 30, 2020, titled "SYSTEMS AND METHODS FOR HOLISTIC LOW CARBON INTENSITY FUEL AND HYDROGEN PRODUCTION," and U.S. Provisional Application No. 63/113, 186, filed Nov. 12, 2020, titled "SYSTEMS AND METHODS FOR HOLISTIC LOW CARBON INTENSITY FUEL AND HYDROGEN PRODUCTION," the disclosures of which are incorporated herein by reference in its entirety.

This application is also a continuation-in-part of U.S. Non-Provisional application Ser. No. 17/392,600, filed Aug. 3, 2021, titled "SYSTEMS AND METHODS FOR HOLISTIC LOW CARBON INTENSITY FUEL PRODUCTION," which claims priority to U.S. Provisional Application No. 63/061,162, filed Aug. 4, 2020, titled "SYSTEMS AND METHODS FOR HOLISTIC LOW CARBON INTENSITY FUEL PRODUCTION," U.S. Provisional Application No. 63/066,912, filed Aug. 18, 2020, titled "SYSTEMS AND METHODS FOR HOLISTIC LOW CARBON INTENSITY FUEL PRODUCTION," U.S. Provisional Application No. 63/198,626, filed Oct. 30, 2020, titled "SYSTEMS AND METHODS FOR HOLISTIC LOW CARBON INTENSITY FUEL AND HYDROGEN PRODUCTION," and U.S. Provisional Application No. 63/113,186, filed Nov. 12, 2020, titled "SYSTEMS AND METHODS FOR HOLISTIC LOW CARBON INTENSITY FUEL AND HYDROGEN PRODUCTION," the disclosures of which are incorporated herein by reference in their entireties.

This application is also a continuation-in-part of U.S. Non-Provisional application Ser. No. 17/583,450, filed Jan. 25, 2022, titled "SYSTEMS AND METHODS FOR HOLISTIC LOW CARBON INTENSITY FUEL PRODUCTION," which is a continuation of U.S. Non-Provisional application Ser. No. 17/392,567, filed Aug. 3, 2021, titled "SYSTEMS AND METHODS FOR HOLISTIC LOW CARBON INTENSITY FUEL PRODUCTION," now U.S. Pat. No. 11,270,393, issued Mar. 8, 2022, which claims priority to U.S. Provisional Application No. 63/061,162, filed Aug. 4, 2020, titled "SYSTEMS AND METHODS FOR HOLISTIC LOW CARBON INTENSITY FUEL PRODUCTION," U.S. Provisional Application No. 63/066,912, filed Aug. 18, 2020, titled "SYSTEMS AND METHODS FOR HOLISTIC LOW CARBON INTENSITY FUEL PRODUCTION," U.S. Provisional Application No. 63/198,626, filed Oct. 30, 2020, titled "SYSTEMS AND METHODS FOR HOLISTIC LOW CARBON INTENSITY FUEL AND HYDROGEN PRODUCTION," and U.S. Provisional Application No. 63/113,186, filed Nov. 12, 2020, titled "SYSTEMS AND METHODS FOR HOLISTIC LOW CARBON INTENSITY FUEL AND HYDROGEN PRODUCTION," the disclosures of which are incorporated herein by reference in their entireties.

This application is also a continuation-in-part of U.S. Non-Provisional application Ser. No. 17/392,622, filed Aug. 3, 2021, titled "SYSTEMS AND METHODS FOR HOLISTIC LOW CARBON INTENSITY FUEL AND ETHANOL PRODUCTION," which claims priority to U.S. Provisional Application No. 63/061,162, filed Aug. 4, 2020, titled "SYSTEMS AND METHODS FOR HOLISTIC LOW CARBON INTENSITY FUEL PRODUCTION," U.S. Provisional Application No. 63/066,912, filed Aug. 18, 2020, titled "SYSTEMS AND METHODS FOR HOLISTIC LOW CARBON INTENSITY FUEL PRODUCTION," U.S. Provisional Application No. 63/198,626, filed Oct. 30, 2020, titled "SYSTEMS AND METHODS FOR HOLISTIC LOW CARBON INTENSITY FUEL AND HYDROGEN PRODUCTION," and U.S. Provisional Application No. 63/113, 186, filed Nov. 12, 2020, titled "SYSTEMS AND METHODS FOR HOLISTIC LOW CARBON INTENSITY FUEL AND HYDROGEN PRODUCTION," the disclosures of which are incorporated herein by reference in their entireties.

This application is also a continuation-in-part of U.S. Non-Provisional application Ser. No. 17/392,588, filed Aug. 3, 2021, titled "SYSTEMS AND METHODS FOR HOLISTIC LOW CARBON INTENSITY FUEL PRODUCTION," which claims priority to U.S. Provisional Application No. 63/061,162, filed, Aug. 4, 2020, titled "SYSTEMS AND METHODS FOR HOLISTIC LOW CARBON INTENSITY FUEL PRODUCTION," U.S. Provisional Application No. 63/066,912, filed Aug. 18, 2020, titled "SYSTEMS AND METHODS FOR HOLISTIC LOW CARBON INTENSITY FUEL PRODUCTION," U.S. Provisional Application No. 63/198,626, filed Oct. 30, 2020, titled "SYSTEMS AND METHODS FOR HOLISTIC LOW CARBON INTENSITY FUEL AND HYDROGEN PRODUCTION," and U.S. Provisional Application No. 63/113,186, filed Nov. 12, 2020, titled "SYSTEMS AND METHODS FOR HOLISTIC LOW CARBON INTENSITY FUEL AND HYDROGEN PRODUCTION," the disclosures of which are incorporated herein by reference in their entireties.

Although particular terms and concepts are incorporated in the present disclosure, Applicant notes that the disclosed terms and concepts are exclusively utilized in a descriptive capacity and should not therefore be construed or interpreted as limiting in any way. Particular embodiments and aspects of the disclosed systems, methods and processes have been described in detail with particular reference to the illustrated embodiments. However, Applicant notes that it will be apparent that numerous and various modifications and alterations may be introduced and performed within the spirit and scope of the embodiments of the systems, methods and processes described herein, and such modifications and alterations are to be considered equivalents and within the breadth and scope of the instant disclosure.

What is claimed is:

1. A method to provide low carbon intensity transportation fuel, the low carbon intensity transportation fuel obtained through one or more targeted reductions of carbon emissions, the method comprising:

determining, via a controller, a carbon intensity threshold to define an upper limit for carbon intensity of transportation fuel to be provided to an end user location;

determining, via the controller, two or more feedstocks that are procured at two or more sources, the two or more feedstocks being selected to reduce carbon emissions associated therewith and thereby maintain the carbon intensity of the transportation fuel below the carbon intensity threshold, at least one of the two or more sources being a regenerative farm, a feedstock from the regenerative farm being a crop, the crop being one or more of corn, soy beans, or other vegetables or grains including sufficient amounts of oil;

determining, via the controller, a transportation pathway to transport the two or more feedstocks from the source to a transportation fuel production facility, the transportation pathway being selected to reduce carbon emissions associated therewith and thereby maintain the carbon intensity of the transportation fuel below the carbon intensity threshold;

determining, via the controller, one or more transportation fuel production processes to reduce carbon emissions and thereby maintain the carbon intensity of the transportation fuel below the carbon intensity threshold, the one or more transportation fuel production processes selected from a group including: powering at least a portion of transportation fuel production facility equipment with electricity generated proximal to the transportation fuel production facility through a renewable source, burning renewable natural gas in a transportation fuel production facility furnace, generating steam through renewable natural gas-fed boilers, and sequestering carbon dioxide produced during the transportation fuel production process;

determining, via the controller, a distribution pathway to transport a quantity of the transportation fuel from the transportation fuel production facility to the end user location, the distribution pathway being selected to reduce carbon emissions associated therewith and thereby maintain the carbon intensity of the transportation fuel below the carbon intensity threshold;

pre-processing the feedstock from the regenerative farm, via crushed crop segregates, to thereby form oil;

processing the oil into renewable transportation fuel together with operating the selected one or more transportation fuel production processes;

blending the renewable transportation fuel with an additional transportation fuel, thereby to produce a transportation fuel;

determining, via the controller, the carbon intensity of the transportation fuel based on a carbon intensity of procurement of the selected feedstock at the source, a carbon intensity of transportation of the feedstock from the source to the transportation fuel production facility by use of the selected transportation pathway, a carbon intensity of processing the feedstock into transportation fuel together with operation of the one or more transportation fuel production processes, and a carbon intensity of transportation of the quantity of transportation fuel to the end user location by use of the selected distribution pathway;

verifying that the carbon intensity of the transportation fuel remains below the carbon intensity threshold for the transportation fuel to be provided to the end user location;

generating an identifying record including one or more of (a) the carbon intensity of the transportation fuel or (b) carbon intensity of a selected feedstock, transportation pathway, one or more transportation fuel production processes, and distribution pathway associated with the transportation fuel; and outputting the transportation fuel through the selected distribution pathway as low carbon intensity transportation fuel.

2. The method according to claim 1, wherein the transportation fuel production facility comprises a refinery, and wherein one of the two or more feedstocks is selected from a hydrocarbon source.

3. The method according to claim 2, further comprising: processing the feedstock from the hydrocarbon source into the additional transportation fuel together with operating the selected one or more transportation fuel production processes.

4. The method according to claim 1, wherein the transportation fuel comprises one or more of diesel, renewable diesel, or ultra-low CI diesel, and wherein the step of processing of the oil produces the one or more diesel, renewable diesel, or ultra-low CI diesel.

5. The method according to claim 1, wherein the pre-processing further produces sustainable meal for use in food or feed products.

6. The method according to claim 1, wherein the transportation fuel comprises one or more of (a) a carbon-neutral transportation fuel or (b) substantially free from carbon fuel in relation to manufacturing and transporting the transportation fuel.

7. The method according to claim 1, wherein one or more of the transportation pathway or the distribution pathway uses one or more of electric power generated from wind energy, electric power generated from solar energy, electric power generated by a hydroelectric generator, electric power generated by a geothermal power generator, or renewable diesel, and the transportation pathway is selected from the group consisting of rail, vehicle, and barge.

8. The method according to claim 1, wherein electricity generated by a renewable source includes electricity generated by one or more of a wind turbine, a solar array, geothermal power generator, a hydroelectric generator, or a stationary fuel cell power system.

9. The method according to claim 1, wherein the carbon intensity associated with procuring the selected feedstock at the source includes a carbon intensity of the selected feedstock and a carbon intensity for providing the feedstock at the source.

10. The method according to claim 1, wherein the transportation fuel production facility is co-located with or proximal to one or more of the one or more sources.

11. A system to operate a transportation fuel production facility for distribution of a low carbon intensity (CI) transportation fuel therefrom and obtained through one or more targeted reductions of carbon emissions (CE), the system comprising:

a controller to control one or more various transportation fuel production processes to be operated at one or more transportation fuel production facilities, the controller including one or more processors and memory storing instructions, the instructions, when executed by the one or more processors, to:

(I) determine a feedstock CI for each of one or more available feedstocks from one or more available feedstock sources to be supplied to the one or more transportation fuel production facilities from one or more available feedstock transportation pathways, the one or more available feedstock sources including a regenerative farm and the one or more available feedstocks including a crop from the regenerative farm, (II) for each one or more available feedstocks:
  (a) determine a feedstock transportation CI for each of one or more available feedstock transportation pathways based on:
    (1) a volume of a feedstock transportation pathway,
    (2) fuel type utilized by the feedstock transportation pathway, and
    (3) distance to travel to the one or more transportation fuel production facility,
  (b) determine a transportation fuel production process CI for each of one or more transportation fuel production processes based on:
    (1) one or more available transportation fuel production processes available at the one or more transportation fuel production facilities, one of the one or more available transportation fuel production processes including pre-processing the feedstock, via crushing crop segregates, thereby to form oil,
    (2) a type of feedstock of the one or more available feedstocks,
    (3) a type of oil formed during pre-processing of the type of feedstock, and
    (3) a yield of each one or more available transportation fuel production processes,
  (c) determine a utilities CI for each of one or more utilities based on:
    (1) a type of utility to be used during a transportation fuel production process and
    (2) a utilities' source,
  (d) determine a transportation fuel distribution CI for each of one or more available transportation distribution pathways based on:
    (1) a volume of a transportation fuel distribution pathway,
    (2) a type of the transportation fuel distribution pathway,
    (3) fuel type utilized by the transportation fuel distribution pathway, and
    (4) distance to travel for a delivery of transportation fuel,
  (e) determine a set of combinations, each of the set of combinations including:
    (1) one or more available feedstocks,
    (2) one or more available feedstock transportation pathways,
    (3) one or more transportation fuel production processes of one or more transportation fuel production facilities,
    (4) one or more utilities, and
    (5) one or more available transportation fuel distribution pathways, and
  (f) determine a total CI for each of the set of combinations based on:
    (1) a volume of the one or more available feedstocks,
    (2) a yield from the one or more transportation fuel production processes,
    (3) the determined feedstock CI,
    (4) the determined feedstock transportation CI,
    (5) the determined transportation fuel production process CI,
    (6) the determined utilities CI, and
    (7) the determined transportation fuel distribution CI,
  (III) determine a final selection from the set of combinations including a total CI less than or equal to a threshold CI, the threshold CI being defined as an upper limit of CI in providing transportation fuel to an end user location that qualifies the transportation fuel as a low CI transportation fuel, the final selection including:
    (a) a selected one or more available feedstocks,
    (b) a selected one or more feedstock transportation pathways,
    (c) a selected one or more transportation fuel production processes of one or more transportation fuel production facilities,
    (d) a selected one or more utilities, and
    (e) a selected one or more transportation fuel distribution pathways,
  (IV) in response to the final selection, transmit a feedstock request based on the selected one or more available feedstocks and the selected one or more feedstock transportation pathways,
  (V) in response to a determined reception of the selected one or more available feedstock at the one or more transportation fuel production facilities, initiate, at the controller, the selected one or more transportation fuel production processes of the one or more transportation fuel production processes, and the selected one or more utilities to operate the selected one or more transportation fuel production processes, thereby to transform the selected one or more available feedstock to transportation fuel, and
  (VI) in response to determination of completion of the selected one or more transportation fuel production processes, transmit a delivery request of the transportation fuel via the selected one or more transportation fuel distribution pathways.

12. The system according to claim 11, wherein the determination of the feedstock CI further includes one or more of:
  (a) a volume of each of the one or more available feedstocks,
  (b) a type of feedstock of each of the one or more available feedstocks,
  (c) a type of fuel utilized by equipment at the feedstock source,
  (d) a type of fertilizer utilized for the feedstock,
  (e) a location of each of the one or more available feedstock, and
  (f) regenerative farming operations utilized at the feedstock source.

13. The system according to claim 11, wherein the determination of the total CI is further based on a transportation fuel storage tank CI and the memory further has instructions to:
  (a) determine the transportation fuel storage tank CI based on:
    (1) a time the transportation fuel will be stored in each of the one or more transportation fuel storage tanks,
    (2) a time and power associated with regulating the temperature of each of the one or more transportation fuel storage tanks, and
    (3) an estimated volume associated with emissions associated with each of the one or more transportation fuel storage tanks.

14. The system according to claim 11, wherein the one or more transportation fuel production processes include options to:
 (a) provide electrical power for the transportation fuel plant through renewable sources, the renewable sources comprising one or more of wind, solar, hydroelectric, geothermal, or hydrogen,
 (b) employ renewable fuels in boilers and fired heaters of the transportation fuel plant, the renewable fuels comprising one or more of renewable diesel or renewable natural gas, and
 (c) sequester carbon dioxide produced during the one or more transportation fuel production processes.

15. The system according to claim 11, wherein the determination of the final selection from the set of combinations is based on:
 (a) the total CI,
 (b) a time of availability of each of the one or more available feedstocks,
 (c) a time for delivery to the transportation fuel production facility by each of the one or more feedstock transportation pathway,
 (d) a time to process one or more available feedstock utilizing each of the one or more transportation fuel production processes, and
 (e) a length of time to deliver, from the transportation fuel production facility to an end user, transportation fuel by each of the one or more transportation fuel distribution pathways.

16. The system according to claim 11, wherein the memory further has instructions to:
 (a) in response to the determined reception of the selected one or more available feedstocks at the transportation fuel production facility:
  (1) determine actual feedstock CI for the selected one or more available feedstocks,
  (2) determine actual feedstock transportation CI for the selected one or more feedstock transportation pathways,
  (3) in response to a determination of an increase of the combined CI of the actual feedstock CI and actual feedstock transportation CI in relation to the combination of the determined feedstock CI and the determined feedstock transportation CI:
   (A) select one or more different transportation fuel production processes, one or more different utilities, or one or more different transportation fuel distribution pathways to maintain total CI.

17. The system according to claim 16, wherein the memory further has instructions to:
 (a) in response to determination of completion of the selected one or more transportation fuel production processes:
  (1) determine actual transportation fuel production process CI for the selected one or more transportation fuel production processes,
  (2) determine actual utility CI for the selected one or more utilities, and
  (3) in response to a determination of an increase of the combined CI of the actual transportation fuel production process CI and actual utility CI in relation to the combination of the determined transportation fuel production process CI and determined utilities CI:
   (A) select one or more different transportation fuel distribution pathways to maintain total CI.

18. The system according to claim 17, wherein the memory further has instructions to:
 (a) in response to determination of completion of the selected one or more transportation fuel distribution pathways:
  (1) determine actual CI for:
   (A) the selected one or more available feedstocks,
   (B) a completed one or more feedstock transportation pathways,
   (C) a completed one or more transportation fuel production processes,
   (D) one or more utilities used to operate the completed one or more transportation fuel production processes, and
   (E) a completed one or more transportation fuel distribution pathways,
  (2) determine actual total CI based on:
   (A) an actual transportation fuel yield,
   (B) an actual transportation fuel volume,
   (C) the actual CI for the completed one or more feedstock transportation pathways,
   (D) the actual CI for the completed one or more transportation fuel production processes,
   (E) the actual CI for the one or more utilities used to operate the completed one or more transportation fuel production processes, and
   (F) the actual CI for the completed one or more transportation fuel distribution pathways, and
  (3) transmit an audit report including the actual CI for each selection and the actual total CI.

19. A controller to operate one or more transportation fuel production facilities for distribution of a low carbon intensity (CI) transportation fuel therefrom and obtained through one or more targeted reductions of carbon emissions (CE), the controller comprising:
 a first input/output in signal communication with a procurement computing device, such that the controller is configured to:
  determine a selection of one or more available feedstocks, a selection of one or more feedstock transportation pathways, a selection of one or more transportation fuel production processes at one or more transportation fuel production facilities, a selection of one or more utilities, and a selection of one or more transportation fuel distribution pathways, each selection based on:
   a determination of feedstock CI of one or more blends of the one or more available feedstocks based on volume and type of feedstock and based on a CI associated with procuring a feedstock, at least one of the one or more available feedstocks comprises a crop from a regenerative farm,
   a determination of feedstock transportation CI of one or more feedstock transportation pathways based on delivery distance and fuel type of the feedstock transportation pathway,
   a determination of transportation fuel production process CI of one or more transportation fuel production processes at one or more transportation fuel production facilities based on the type of transportation fuel production process, the volume and type of feedstock, and the length of time of the transportation fuel production process, at least one of the one or more transportation fuel production processes including pre-processing a feedstock, via crushing of crop segregates, thereby to produce an oil, a determination of utility CI of one or more utilities based on the type of utility utilized to operate the one or more transportation fuel production processes and a distance the one or more utilities travel to the one or more transportation fuel production processes, a determination of transportation fuel distribution CI of one or more transportation fuel distribution pathways based on delivery distance and fuel type of a transportation fuel distribution pathway, and a determination of one or more total CIs less than the threshold CI, the total CIs based on varying combinations of the determinations of CI, in response to the selection of the one or more available feedstocks, the selection of one or more feedstock transportation pathways, the selection of one or more transportation fuel production processes at one or more transportation fuel production processes, the selection of one or more utilities, and the selection of one or more transportation fuel distribution pathways:

transmit a feedstock request to the procurement computing device, the feedstock request including the selection of the one or more available feedstocks and the selection of the one or more feedstock transportation pathways;

a second input/output in signal communication with a transportation fuel production facility controller, the transportation fuel production facility controller to control one or more various transportation fuel production processes to be operated at the one or more transportation fuel production facilities, such that the controller is configured to:

in response to a determined reception of the selected one or more available feedstock at the one or more transportation fuel production facilities:

determine actual feedstock CI and actual feedstock transportation CI, in response to a determination that the actual feedstock CI and actual feedstock transportation CI has increased in relation to the determined feedstock CI and determined feedstock transportation CI, determine one or more of a new selection of one or more transportation fuel production processes, a new selection of one or more utilities, and a new selection of one or more transportation fuel distribution pathways to maintain total CI, and initiate, at the transportation fuel production facility controller, the selected one or more transportation fuel production processes at the one or more transportation fuel production facilities and the selected one or more utilities to operate the selected one or more transportation fuel production processes at the one or more transportation fuel production facilities, thereby to transform the selected one or more available feedstocks to transportation fuel; and a third input/output in signal communication with a distribution computing device such that the controller is configured to:

in response to determination of completion of the selected one or more transportation fuel production processes at the selected one or more transportation fuel production facilities:

determine an actual transportation fuel production process CI and an actual utility CI, in response to a determination that the actual transportation fuel production process CI and actual utility CI has increased in relation to the determined transportation fuel production process CI and determined utility CI, determine one or more new selections of one or more transportation fuel distribution pathways, and transmit a delivery request of the transportation fuel via the selection of the one or more transportation fuel distribution pathways to the distribution computing device.

20. The controller according to claim 19, wherein the one or more transportation fuel production processes include offsetting practices and wherein the offsetting practices include transportation fuel production processes to:

provide electrical power for the one or more transportation fuel production facilities through renewable sources, the renewable sources comprising wind, solar, hydroelectric, geothermal, or hydrogen fuel cells, employ renewable fuels in boilers and fired heaters of the transportation fuel production facility, the renewable fuels comprising renewable diesel and renewable natural gas, sequester one or more of carbon monoxide or carbon dioxide produced during the one or more transportation fuel production processes, and sequester carbon dioxide produced during the one or more transportation fuel production processes.

21. The controller according to claim 20, wherein sequestering oen or more of carbon monoxide or carbon dioxide produced during the one or more transportation fuel production processes involves the production of low intensity hydrogen.

22. A method to provide low carbon intensity transportation fuel, the low carbon intensity transportation fuel obtained through one or more targeted reductions of carbon emissions, the method comprising:

determining a carbon intensity threshold to define an upper limit for carbon intensity of transportation fuel to be provided to an end user location;

determining two or more feedstocks that are procured at two or more sources, the two or more feedstock being selected to reduce carbon emissions associated therewith and thereby maintain the carbon intensity of the transportation fuel below the carbon intensity threshold, at least one of the two or more sources being a regenerative farm, a feedstock from the regenerative farm being a crop, the crop being one or more of corn, soy beans, or other vegetables or grains including sufficient amounts of oil;

determining a transportation pathway to transport the two or more feedstocks from the source to a transportation fuel production facility, the transportation pathway being selected to reduce carbon emissions associated therewith and thereby maintain the carbon intensity of the transportation fuel below the carbon intensity threshold;

determining one or more transportation fuel production processes to reduce carbon emissions and thereby maintain the carbon intensity of the transportation fuel below the carbon intensity threshold, the one or more transportation fuel production processes selected from a group including: powering at least a portion of transportation fuel production facility equipment with electricity generated proximal to the transportation fuel production facility through a renewable source, burning renewable natural gas in a transportation fuel production facility furnace, generating steam through renewable natural gas-fed boilers, and sequestering carbon dioxide produced during the transportation fuel production process;

determining a distribution pathway to transport a quantity of the transportation fuel from the transportation fuel production facility to the end user location, the distribution pathway being selected to reduce carbon emissions associated therewith and thereby maintain the carbon intensity of the transportation fuel below the carbon intensity threshold;

pre-processing the feedstock from the regenerative farm, via crushing crop segregates, thereby to produce oil;

processing the oil into renewable transportation fuel together with operating the selected one or more transportation fuel production processes;

blending the renewable transportation fuel with an additional transportation fuel, thereby to produce a transportation fuel;

determining the carbon intensity of the transportation fuel associated with procuring the selected feedstock at the source, associated with transporting the feedstock from the source to the transportation fuel production facility by use of the selected transportation pathway, associated with processing the feedstock into transportation fuel transportation fuel together with operating the one or more transportation fuel production processes, and associated with transporting the quantity of transportation fuel to the end user location by use of the selected distribution pathway;

verifying that the carbon intensity of the transportation fuel remains below the carbon intensity threshold for the transportation fuel to be provided to the end user location;

generating an identifying record including one or more of (a) the carbon intensity of the transportation fuel or (b) carbon intensity of a selected feedstock, transportation pathway, one or more transportation fuel production processes, and distribution pathway associated with the transportation fuel; and outputting the transportation fuel through the selected distribution pathway as low carbon intensity transportation fuel.

23. The method according to claim 22, wherein the transportation fuel production facility comprises a refinery, and wherein one of the two or more feedstocks is selected from a hydrocarbon source.

24. The method according to claim 23, further comprising:

processing the feedstock from the hydrocarbon source into the additional transportation fuel together with operating the selected one or more transportation fuel production processes.

25. The method according to claim 22, wherein the pre-processing further produces sustainable meal for use in food or feed products.

26. The method according to claim 22, wherein the transportation fuel comprises one or more of (a) a carbon-neutral transportation fuel or (b) substantially free from carbon in relation to manufacturing and transporting the transportation fuel.

27. The method according to claim 22, wherein one or more of the transportation pathway or the distribution pathway uses one or more of electric power generated from wind energy, electric power generated from solar energy, electric power generated by a hydroelectric generator, electric power generated by a geothermal power generator, or renewable diesel, and the transportation pathway is selected from the group consisting of rail, vehicle, and barge.

28. The method according to claim 22, wherein electricity generated by a renewable source includes electricity generated by one or more of a wind turbine, a solar array, geothermal power generator, a hydroelectric generator, or a stationary fuel cell power system.

29. The method according to claim 22, wherein the carbon intensity associated with procuring the selected feedstock at the source includes a carbon intensity of the selected feedstock and a carbon intensity for providing the feedstock at the source.

30. The method according to claim 22, wherein the transportation fuel production facility is co-located with or proximal to one or more of the one or more sources.

* * * * *